United States Patent
Mishra et al.

(10) Patent No.: US 10,964,408 B2
(45) Date of Patent: Mar. 30, 2021

(54) METHOD, COMPUTER-ACCESSIBLE MEDIUM AND SYSTEM FOR BASE-CALLING AND ALIGNMENT

(75) Inventors: Bhubaneswar Mishra, New York, NY (US); Giuseppe Narzisi, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/266,662

(22) PCT Filed: Apr. 27, 2010

(86) PCT No.: PCT/US2010/032613
§ 371 (c)(1),
(2), (4) Date: Oct. 27, 2011

(87) PCT Pub. No.: WO2010/129301
PCT Pub. Date: Nov. 11, 2010

(65) Prior Publication Data
US 2012/0116688 A1 May 10, 2012

Related U.S. Application Data

(60) Provisional application No. 61/173,200, filed on Apr. 27, 2009.

(51) Int. Cl.
*G16B 30/00* (2019.01)
*C12Q 1/6869* (2018.01)

(52) U.S. Cl.
CPC ........... *G16B 30/00* (2019.02); *C12Q 1/6869* (2013.01)

(58) Field of Classification Search
CPC ...................................................... G06F 19/22
See application file for complete search history.

(56) References Cited

U.S. PATENT DOCUMENTS

| | | |
|---|---|---|
| 7,232,656 B2 | 6/2007 | Balasubramanian et al. |
| 2002/0055112 A1 | 5/2002 | Patil et al. |

(Continued)

OTHER PUBLICATIONS

Brockman, W. et al. Quality scores and SNP detection in sequencing-by-synthesis systems. Genome Research 18, 763-770 (2008).*

(Continued)

*Primary Examiner* — Soren Harward
(74) *Attorney, Agent, or Firm* — Hunton Andrews Kurth LLP

(57) ABSTRACT

Exemplary methods, procedures, computer-accessible medium, and systems for base-calling, aligning and polymorphism detection and analysis using raw output from a sequencing platform can be provided. A set of raw outputs can be used to detect polymorphisms in an individual by obtaining a plurality of sequence read data from one or more technologies (e.g., using sequencing-by-synthesis, sequencing-by-ligation, sequencing-by-hybridization, Sanger sequencing, etc.). For example, provided herein are exemplary methods, procedures, computer-accessible medium and systems, which can include and/or be configured for obtaining raw output from a sequencing platform configured to be used for reading fragment(s) of genomes, obtaining reference sequences for the genomes obtained independently from the raw output, and generating a base-call interpretation and/or alignment using the raw output and the reference sequences. For example, a score function can be determined based on information associated with the sequencing platform that can be used to analyze polymorphisms based on the base-call interpretation and/or alignment.

37 Claims, 11 Drawing Sheets

(56) References Cited

U.S. PATENT DOCUMENTS

2004/0053246 A1\* 3/2004 Sorenson .................. 702/20
2005/0221341 A1 10/2005 Shimkets et al.

OTHER PUBLICATIONS

Delcher, A. L. et al. Alignment of whole genomes. Nucleic Acids Research 27, 2369-2376 (1999).\*
Hillier, L. W. et al. Whole-genome sequencing and variant discovery in C. elegans. Nature Methods 5, 183-188 (2008).\*
Horton, P. A branch and bound algorithm for local multiple alignment. Pacific Symposium on Biocomputing 368-383 (1996).\*
Li, H., Ruan, J. & Durbin, R. Mapping short DNA sequencing reads and calling variants using mapping quality scores. Genome Research 18, 1851-1858 (2008).\*
Marth, G. T. et al. A general approach to single-nucleotide polymorphism discovery. Nature Genetics 23, 452-456 (1999).\*
Ossowski, S. et al. Sequencing of natural strains of *Arabidopsis thaliana* with short reads. Genome Research 18, 2024-2033 (2008).\*
Salzberg, S. L., Church, D., DiCuccio, M., Yaschenko, E. & Ostell, J. The genome Assembly Archive: a new public resource. PLoS Biology 2, E285:1273-1275 (2004).\*
Schatz, M. C., Phillippy, A. M., Shneiderman, B. & Salzberg, S. L. Hawkeye: An interactive visual analytics tool for genome assemblies. Genome Biology 8, R34:1-12 (2007).\*
Schmid, K. J. et al. Large-scale identification and analysis of genome-wide single-nucleotide polymorphisms for mapping in *Arabidopsis thaliana*. Genome Research 13, 1250-1257 (2003).\*
Smith, D. R. et al. Rapid whole-genome mutational profiling using next-generation sequencing technologies. Genome Research 18, 1638-1642 (2008).\*
Giddings, M. C., Brumley, R. L., Haker, M. & Smith, L. M. An adaptive, object oriented strategy for base calling in DNA sequence analysis. Nucleic Acids Research 21, 4530-4540 (1993).\*
Chevreux, B. et al. Using the miraEST assembler for reliable and automated mRNA transcript assembly and SNP detection in sequenced ESTs. Genome Res. 14, 1147-1159 (2004).\*
Gordon, D., Abajian, C. & Green, P. Consed: A Graphical Tool for Sequence Finishing. Genome Res. 8, 195-202 (1998).\*
Luque, G. & Alba, E. Metaheuristics for the DNA Fragment Assembly Problem. Int. J. Comput. Intell. Res. 1, 98-108 (2005).\*
Sundquist, A., Ronaghi, M., Tang, H., Pevzner, P. & Batzoglou, S. Whole-genome sequencing and assembly with high-throughput, short-read technologies. PLoS One 2, e484 (2007).\*
Li, R., Li, Y., Kristiansen, K. & Wang, J. SOAP: short oligonucleotide alignment program. Bioinformatics 24, 713-714 (2008).\*
Rougemont, J. et al. Probabilistic base calling of Solexa sequencing data. BMC Bioinformatics 9, 431:1-12 (2008).\*
Illumina, Inc. Genome Analyzer Pipeline Software User Guide. (2008).\*
Smith, A. D., Xuan, Z. & Zhang, M. Q. Using quality scores and longer reads improves accuracy of Solexa read mapping. BMC Bioinformatics 9, 128:1-8 (2008).\*
Stephens, M., Sloan, J. S., Robertson, P. D., Scheet, P. & Nickerson, D. A. Automating sequence-based detection and genotyping of SNPs from diploid samples. Nature Genetics 38, 375-381 (2006).\*
Chevreux, B., Pfisterer, T. & Suhai, S. Automatic Assembly and Editing of Genomic Data. in Genomics and Proteomics: Functional and Computational Aspects 51-65 (Kluwer Academic Publishers, 2000).\*
Kircher, M. & Kelso, J. High-throughput DNA sequencing—concepts and limitations. BioEssays 32, 524-36 (2010).\*
Loman, N. J. et al. Performance comparison of benchtop high-throughput sequencing platforms. Nature Biotechnology 30, 434-439 (2012).\*
Metzker, M. L. Sequencing technologies—the next generation. Nature Reviews Genetics 11, 31-46 (2010).\*
Niedringhaus, T. P., Milanova, D., Kerby, M. B., Snyder, M. P. & Barron, A. E. Landscape of next-generation sequencing technologies. Analytical Chemistry 83, 4327-4341 (2011).\*
Shendure, J. & Ji, H. Next-generation DNA sequencing. Nature Biotechnology 26, 1135-1145 (2008).\*
Illunnina, Inc. Genome Analyzer IIx System Specification. 2009.\*
International Search Report for PCT/US2010/032613 dated Dec. 8, 2010.
International Written Opinion for PCT/US2010/032613 dated Dec. 8, 2010.
B. Ewing et al., "Base-Calling of Automated Sequencer Traces Using Phred. Accuracy Assessment," Genome Research, vol. 8, pp. 175-185, 1998.
B. Ewing et al., "Base-Calling of Automated Sequencer Traces Using Phred. Error Probabilities," Genome Research, vol. 8, pp. 186-194, 1998.
Nyren, P. et al. "Solid Phase DNA minisequencing by an Enzymatic Luminometric Inorganic Pyrophosphate Detection Assay" Annal. Biochem. vol. 208;1, pp. 171-175; 1993.
Ronaghi, M.et al. "PCR-Introduced Loop Structure as Primer in DNA sequencing" Biotechniques, vol. 25;5, pp. 876-884, 1998.
Margulies, M.et al. "Genome Sequencing in Micro-fabricated High-Density Picaoliter Reactors" Nature, vol. 437;15, pp. 376-380, 2005.
Erlich Y., et al. "Alta-Cyclic: a self-optimizing base caller for next-generation sequencing" Nature Methods, vol. 5; 8, pp. 679-682, 2008.
Barany, F. "The Ligase Chain Reaction in a PCR World" PCR Methods Applications., vol. 1;5 pp. 5-16, 1991.
Nickerson, D.A., et al. "Automated DNA Diagnostics Using an ELISA-Based Oligonucleotide Ligation Assay" PNAS, vol. 87; 22, pp. 8923-8927, 1991.
Drmanac, R.,et al. "DNA Sequence Determination by Hybridization: A Strategy for Efficient Large-Scale Sequencing" Science, vol. 260; pp. 1649-1652, 1993.
Broude, N.E., et al. "Enhanced DNA Sequencing by Hybridization" PNAS, vol. 91; 8, p. 3072-3076, 1994.
Levene, M.J., etal. "Zero-Mode Waveguides for Single-Molecule Analysis at High Concentrations" Science, vol. 299, pp. 682-686 2003.
Fologea, D. et al. "Detecting Single Stranded DNA with a Solid State Nanopore" Nano Letters, vol. 5, No. 10, pp. 1905-1909, 2005.
Meller, A. et al., Rapid Nanopore Discrimination Between Single Polynucleotide Molecules, PNAS, vol. 97, No. 3, pp. 1079-1084, 2000.
The International HapMap Consortium, the International HapMap Project, Nature, vol. 426, No. 18, pp. 789-796, 2003.
The International HapMap Consortium, "A Haplotype Map of the Human Genome", Nature, vol. 437, No. 27, pp. 1299-1320, 2005.
M. Stephens and P. Donelly,"A Comparison of Bayesian Methods for Haplotype Reconstruction from Population Genotype Data" Am. J. of Hum. Genet., vol. 73;5, pp. 1162-1169, 2003.
L. Feuk et al., "Structural Variation in the Human Genome" Nature Review Genetics, vol. 7, No. 2, pp. 85-97, 2006.
J.Sebat et al. "Large-Scale Copy Number Polymorphism in the Human Genome" Science, vol. 305, No. 5683, pp. 525-528, 2004.
Efron, B., "Large-scale simultaneous hypothesis testing: the choice of a null hypothesis" J. Am. Statist. Assoc., vol. 99, pp. 96-104, 2004.

\* cited by examiner

FIG. 2

Algorithm 1: Base-caller / – Pseudo code (Beam-Search)

Input: Start base $R_0$, max queue size $K$
Output: Accurate sequence read

```
1  T := ∅;                                        /* Set of leaves */
2  L := {(R_0, g(R_0))};                          /* Set of live nodes (FIFO queue) */
3  while (L ≠ ∅) do
4      Sort (L);                                  /* Sort live nodes based on their score */
5      L := Prune (L, K);                         /* Prune the queue to size K */
6      for (i=1 to min(K, |L|)) do
7          R_j := L.getNext();
8          L := L \ {R_j};
9          for (j+1 to 4) do
                                                  /* Expand (R_j generating R_A,R_T,R_G,R_C */
10             if (R_ij is a leaf) then
11                 T := T ∪ {R_ij};               /* R_ij is a leaf */
12             else
13                 L := L ∪ {R_ij, g(R_ij)};      /* Add to the queue */
14             end
15         end
16     end
17 end
18 return maxR_i ∈ T {g(R_i)};
```

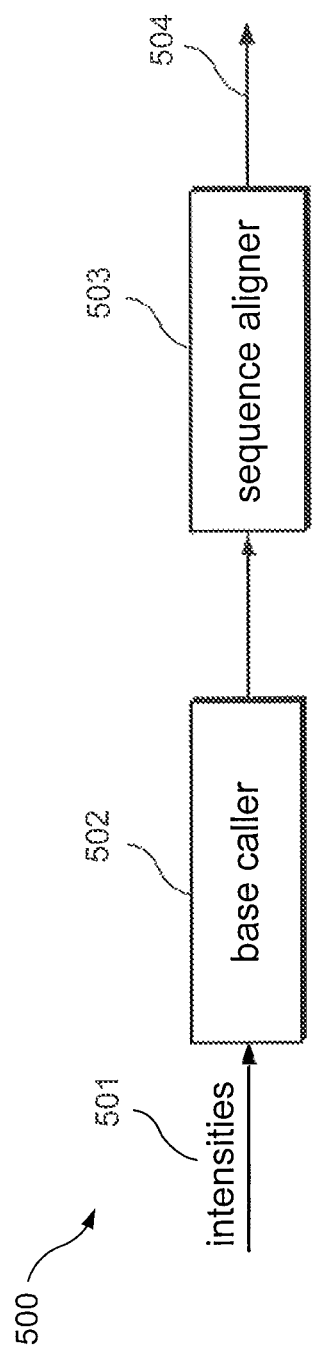
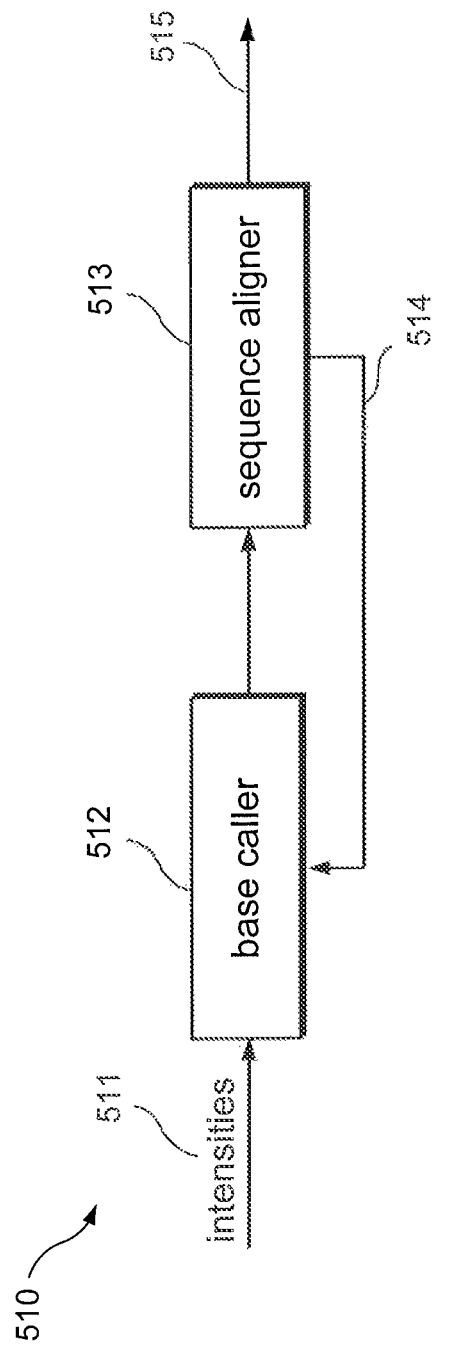

METHOD, COMPUTER-ACCESSIBLE MEDIUM AND SYSTEM FOR BASE-CALLING AND ALIGNMENT

CROSS-REFERENCE TO RELATED APPLICATION(S)

The present application relates to and claims priority from International Patent Application No. PCT/US2010/032613 filed on Apr. 27, 2010, and from U.S. Pat. Application No. 61/173,200 filed Apr. 27, 2009, the entire disclosures of which are hereby incorporated herein by reference. This application also relates to U.S. Provisional Pat. Application No. 61/140,831, filed Dec. 24, 2008, the entire disclosure of which is hereby incorporated herein, by reference.

STATEMENT REGARDING FEDERALLY SPONSORED RESEARCH

The present disclosure was developed, at least in part, using Government support under Contract Project No. F6199 awarded by the National Science Foundation and Contract Project No. F6112 awarded by the National Human Genome Research Institute of the National Institutes of Health. Therefore, the Federal Government may have certain rights in the invention.

FIELD OF THE DISCLOSURE

The present disclosure relates generally to exemplary embodiments of methods, procedures, computer-accessible medium and systems for base calling and alignment, and analyzing polymorphisms based on related base-call interpretation(s) and/or alignment(s) of biological sequences.

BACKGROUND INFORMATION

Currently, there likely exists efforts to develop a relatively inexpensive genome sequencing platform that can be of acceptable accuracy (e.g., about one base error in 10,000 base pairs (bps)) and relatively high-speed (e.g., a turn-around/processing time of less than one day). In order for the sequence reads obtained from such a sequencing platform to be useful in certain biomedical applications, they can usually have to be sufficiently long and accurate, which can thus enable sequence assembly and/or resequencing (e.g., through an alignment against a reference genome, where available). If the reads from a sequencing platform are shorter than certain thresholds, its utility in many biomedical applications can be limited even though the platform can provide a cost and/or throughput advantage. One way to improve the accuracy and/or length of sequence reads from such a platform can be through better statistical algorithms (and/or procedures) for base-calling and/or alignment than heretofore available.

If certain simplifying assumptions about genomes in a human population were to be true, then resequencing and/or alignment tasks can potentially often be made algorithmically trivial and, to some degree, capable of generating useful bio-medical information. For example, if it is possible to be reasonably assured of the correctness of the assembly of the reference genotype sequence (e.g., that the polymorphisms can be relatively rare and uniformly distributed, and that the populations can have very few admixtures of separate ancestries), then it can likely suffice to just position a massive number of short reads that can be aligned to a single (and/or a few, several, bunch, many, etc.) reference sequence(s), which can thus facilitate a relatively non-complicated technology to determine and/or study virtually any individual's genomic make-up.

In the absence of a genuine (acceptable) confidence in these underlying assumptions, there can be a need for, e.g., integrating multiple technologies that can be coupled to computational algorithms in order to accurately detect a wide class of polymorphisms (e.g., single nucleotide polymorphisms (SNPs), copy number variations (CNVs), structural variations (SVs), etc.), confidently characterize the detected polymorphisms, and/or assemble and align the reads to whole genome genotypic and/or haplotypic reference sequences, for example. In order for the relatively less expensive and high-throughput sequencing platforms to be of value to these applications, it can involve improving the statistical algorithms that can be used to interpret raw data from experiments into a base-by-base sequence. For example, in certain sequencing platforms, where the read-lengths may not be short (e.g., in a range from about 100 bps to about 1000 bps), these statistical algorithms can be useful in reducing the corresponding coverage and thus the associated cost.

Previously available sequencing platforms likely fall short of a scalable haplotypic whole-genome technology for which there appears to be a need. For example, such heretofore available technologies usually can generate relatively short genotypic reads (e.g., from about 35 bps to about 300 bps, without haplotypic and locational context), that can be corrupted by errors such as low-quality base-calls and/or compression of homopolymeric runs, and can frequently lack long-range contextual information aside from mate-pair data. These shortcomings can affect the yield and/or speed of the resulting technology and have a debilitating effect on the complexity of the base-calling, alignment and/or assembly algorithms and/or procedures.

To meet the challenges of long-range haplotypic analysis, there may be a need for, e.g., technology and/or algorithm design principles that can go beyond base-by-base reads and take into account the tractability of a computation that can be used to handle the resulting data. Otherwise, a cost improvement and/or throughput gain at the single-base level can be mis-utilized without the intended benefit, when used at the whole-genome level, for example. Sequencing technologies can typically be considered and/or thought of in terms of two extremes. For example, at one extreme can be technologies such as, e.g., Sanger sequencing, which can work by producing a correct index for every base, but can generally extend only over a short range. At the other extreme technologies may be provided that, similarly to many single-molecule and/or nanopore-based sequencers, can aim for (potentially) long reads, but can lack any location information, for example. These and related current and/or anticipated technologies can be generally categorized into three groups, e.g., (i) Short Reads-Low Throughput Technology (e.g. 454, Solexa, Solid, etc.), (ii) Shorter Reads-High Throughput Technology (e.g., Lab-on-chips, Illumina's Flowcell based systems, Raindance, etc.), and (iii) Long Reads and Contextual Reads Technology (e.g., PacificBio, NanoBioMatrix, Oxford Nanopore, Nanopore Sequencing, etc.).

Certain proposals for generating short sequence reads from genomes relatively quickly, inexpensively and in large amounts have likely led to commercial equipment that can be used accordingly. Before such proposals and associated equipment, dideoxynucleotide termination DNA sequencing technology, introduced by Fred Sanger in 1977 and known as the "Sanger Sequencing" technology, had likely been the routine procedure for large-scale sequencing. (See, e.g., Smith L. M. et al., *Fluorescence Detection in Automated DNA Sequence Analysis*, Nature, 321, 6071, 674-679 (1986)). Since its introduction in 1977, Sanger sequencing technology has been improved upon, e.g., streamlined with better latency and higher throughput via improved, parallel and relatively rapid sorting of fragments using capillary gel electrophoresis, addressing some of the inherent limitations posed by Joule-heating during fragment separation using slab gels, for example. However, despite such improvements, at least two limitations can remain. For example, the upper limit of read-lengths can be about one Kb, and the reads can have no associated contextual information (e.g., chromosomal location and/or haplotypic disambiguation).

Several intensive parallel sequencing methods have been proposed to address some of these issues. However, while some of these proposed methods may provide lower latency and/or higher throughput at a relatively lower cost, such proposed methods may not have improved the read lengths nor provided for any contextual information. For example, one such massively parallel sequencing technology can be "Sequencing by Synthesis Pyrosequencing," (see, e.g., Nyren, P. et al., *Solid Phase DNA minisequencing by an Enzymatic Luminometric Inorganic Pyrophosphate Detection Assay*, Annal Biochem 208, 1, 171-175 (1993); Ronaghi, M. et al., *PCR-Introduced Loop Structure as Primer in DNA sequencing*, Biotechniques, 25, 5, 876-884 (1998); and Margulies, M. et al., *Genome Sequencing in Micro-fabricated High-Density Picoliter Reactors*, Nature, 437, 7057, 376-380 (2005). In addition, a goal of Pacific Bioscience can be to create a technology that can read up to about 5 Kb without increasing the associated cost. While such technology can potentially have a positive effect on certain approaches and algorithms, Pacific Biosciences' technology can provide only a limited improvement as it can still lack long-range information, for example.

In pyrosequencing procedures, which can include a sequencing-by-synthesis technology, upon nucleotide incorporation by the polymerase, the released pyrophosphate can be converted to adenosine triphosphate (ATP) by action of the enzyme sulfurylase using an energy source to convert luciferin to oxyluciferin and light. Because, in sequencing by synthesis, during each cycle, a single nucleotide species (e.g., A, T, C or G) can be used for querying, detection of the emitted light in each reaction cycle can provide the information as to which particular base (and how many) was incorporated in such reaction cycle. By combining the information from many successive cycles, it is possible to read a large number of sequences in parallel. These sequencing technologies can be found in certain applications, such as, e.g., SNP-calling, CNV-detection, serial analysis of gene expression (SAGE) profiling, cDNA sequencing, nucleasome positioning and metagenomics. However, such sequencing technologies can have certain shortcomings in various applications, including applications addressing population genomics, personal genomics and/or genomics-based individualized medicine, which can likely be due to associated length limitations and/or lack of contextual information.

For example, the pyrosequencing procedures can occur in the 454 GS-20 sequencing instruments (see, e.g., Margulies, M. et al., *Genome Sequencing in Microfabricated Serial Analysis of Gene Expression High-Density Picolitre Reactors*, Nature, 437, 7057, 376-380 (2005)). Such instrument can integrate and parallelize the process, e.g., from library construction to sequence detection, Starting with a genomic library of 500 bps-long fragments, the ends of such fragments can first be repaired, then ligated with 454-specific linkers, and then coupled to Sepharose beads with covalently linked complementary oligoes that can hybridize to the fragment library's ligated linkers, for example. The bead/DNA complexes can be emulsified in oil suspension containing aqueous PCR reagents in order for PCR amplifications to occur for each library-fragment producing many like PCR products attached to the same bead. Pyrosequencing reactions can then be performed on these PCR products simultaneously so long as sequence detection can be achieved reliably and synchronously. For example, the pyrosequencing reactions can be carried out on the beads once they are suitably arrayed on a PicoTiterPlate (PTP) device with sensors (e.g., fused optical fibers) designed on to them. It is possible to then deconvolve the optical data into about 400,000 sequencing reads of 500 bps reads (e.g., about 200 Mb of data in total), over the course of a few hours.

However, similarly to the other related technologies, 454-platform's read-length can be relatively short (e.g., only about 500 bps) and the 400,000 fragments can lack contextual information. In addition, because in each cycle there can be no unambiguous way of determining exactly how many bases get incorporated, if the genomic fragment has a run of a single nucleotide base, the 454-instrument cannot tell the run length, and thus cannot produce a compression of the homopolymeric run to a single base, for example.

In order to circumvent the problem of compression of homopolymeric runs, it is possible to utilize a more complex reversible dye-terminator chemistry, such as used in a platform by, e.g., Solexa, Ltd. Starting with a library of genomic fragments, which can then be linker ligated, they can be amplified in situ following hybridization to complementary oligoes covalently linked to a flow cell surface. For example, the fragments can then be amplified into clusters of PCR products, denatured, annealed with sequencing primers, and then read by a sequencing-by-synthesis approach to detect the 3'-blocked fluorescent-labeled nucleotide incorporated in a reaction cycle. Using this approach, a Solexa instrument can read about 60 million sequences, each can have a read-length of no larger than about 50 bps. Similarly to other technologies, the read-lengths from this technology can be relatively short and have no contextual information. Thus, despite being able to read almost 1× coverage of a genotypic human genome in a single run, these reads can fail to assemble and provide any meaningful information. Even in relatively simple resequencing applications, a lack of contextual information can pose significant difficulties/obstacles in placing the short sequence reads in the reference sequence efficiently and accurately.

In 454-, Solexa's technologies and other similar technologies, the problem that limits the length of the sequence reads (and/or accurate base calling) can be primarily due to, e.g., (i) unavoidable failure in synchronization among the relatively small number of like molecules being queried in parallel, and (ii) their inability to survive in toto until the completion of succession of the necessary read queries. For example, the first problem can manifest itself in terms of corruption due to lead and lag reads (increasing a structured noise), and the second problem can manifest itself in terms of loss of signal due to fading (decreasing the signal). The resulting loss/reduction in signal-to-noise ratio (SNR), which can deteriorate exponentially, can make it virtually impossible to read a sequence beyond a certain limited read-length. It is possible to facilitate the read-length of the Solexa technology by modeling these stochastic processes by a random-walk model whose parameters can be learned automatically from the reads of few calibrating DNA molecules. (See, e.g.; Erlich Y., et al., *Alta-Cyclic: a self-optimizing base caller for next-generation sequencing*" Nat Methods, 5, 8, 679-82 (2008)).

In addition to these two platforms, there can be other related technologies, such as ligation-based sequencing (e.g., building on genotyping methods used in ligation-chain-reaction (LCR) and oligonucleotide ligation assay (OLA)), sequencing by hybridization (e.g., a variant called single molecule approach to sequencing by hybridization (SMASH) which can replace array-based hybridization with hybridization to single molecules that can then be queried on a surface), sequencing with zero-mode waveguide, and nanopore sequencing approaches, for example. (See, e.g., Barany, F., *The Ligase Chain Reaction in a PCR World*, PCR Methods Appl., 1, 1, 5-16 (1991): Nickerson, D. A., et al., *Automated DNA Diagnostics Using an ELISA-Based Oligonucleotide Ligation Assay*, PNAS, 87, 22, 8923-8927 (1991); Drmanac, R., et al., *DNA Sequence Determination by Hybridization: A Strategy for Efficient Large-Scale Sequencing*, Science, 260, 5114, 1649-1652, (1993); Broude, N. E., et al., *Enhanced DNA Sequencing by Hybridization*, PNAS, 91, 8, 3072-3076 (1994); Levene, M. J., et al., *Zero-Mode Waveguides for Single-Molecule Analysis at High Concentrations*, Science, 299, 5607, 682-686 (2003); Fologea, D. et al., *Detecting Single Stranded DNA with a Solid State Nanopore*, Nano Letter, 5, 10, 1905-1909 (2005); and Meller, A., et al., *Rapid Nanopore Discrimination Between Single Polynucleotide Molecules*, PNAS, 97, 3, 1079-1084, (2000)).

With the particular successful completion of the human genome project (HGP), it likely has been generally assumed that, with access to a reference human genome sequence, it would be relatively easy to catalog individual genomic differences relative to the reference genome sequence. For example, it has been generally assumed that the remaining significant challenges would only be in terms of designing (i) inexpensive experimental setups targeting relatively few and manageably small regions of polymorphic sites (e.g., about 30,000 haplotype blocks each encompassing no more than about 10 haplotypes), and (ii) efficient algorithmic solutions for interpreting a massive amount of population-wide polymorphism data. However, several implicit assumptions and hitherto unknown facts can impede progress along this direction. For example, currently available reference genome sequences can generally provide only genotypic information and can remain to be validated as to its suitability in representing humans in a universal manner.

Additionally, the possible categories of dominant polymorphisms and their distributions likely have not been satisfactorily cataloged. Further, haplotype data from a population can likely only be collected in many non-contextual short-range fragments that can provide no meaningful long-range structural information. Moreover, such short-range data can likely have to be phased statistically from population-wide distributions and with an inferred (and/or assumed) distribution of recombination sites, which can differ significantly from the reality, for example.

In attempting to exacerbating these and other fundamental hurdles, it is possible to also encounter an added difficulty of dealing with relatively high intractable computational problems, which can arise from having to interpret non-contextual short-range data from many individuals and many subpopulations with unknown population stratification relative to a genotypic reference sequence. Certain developments can circumvent these difficulties by, e.g., focusing on every individual in a population one at a time and by reconstructing their haplotypic genome sequences relatively accurately (e.g., SMASH sequencing-by-hybridization technology). Such technologies can do so without the reference to other genome sequence(s) from another (e.g., in a trio or from a sibling) or many other individual(s) from a population.

For example, with the use of currently available non-contextual short-range sequencing platforms, it is possible to map the sequence reads to the reference genome using a relatively efficient and accurate sequence alignment algorithm under an assumption that reads will contain few localized polymorphisms and are nearly identical to their corresponding sequence in the reference genome. In practice, it is possible to use a low-coverage (e.g., about 2 or 3×) sequencing project to generate a sufficient number of reads to characterize a large number of positional variations on the target genome. However, the entire approach relies on the simplifying assumption that, although the "next-generation" sequencing technologies can be unsuitable for de novo genome sequencing, they can be adapted to genome resequencing, in which assumption as to how haplotypic ambiguities and structural variations can be suitably handled can be unclear.

Further, in studies based on a resequencing approach, it may have been assumed that it can be of no significance to ignore most of the different sequence variations that any individual carries, and that it can suffice to concentrate efforts on important common variations, such as those carried by a relatively large fraction (e.g., greater than or equal to about 5%) of individuals in a population, as only these are likely assumed to be disease associated. Following this reasoning, it is possible to first characterize the frequent genetic variations by short-range resequencing of a limited number of randomly selected individual(s) from populations and, using this information, from genome-wide genotyping, to determine allelic types for any previously characterized variation sites in the target genome(s). For example, this approach has been an integral component of the HapMap Project, which focuses on mapping common SNPs. (See, e.g., The International HapMap Consortium, *The International HapMap Project*, Nature, 426, 18, 789-796 (2003); and The International HapMap Consortium, *A Haplotype Map of the Human Genome*, Nature, 437, 27, 1299-1320 (2005)).

The HapMap project has been implemented in two primary phases. First, using the genomes of 269 individuals from different populations, about a million SNPs were mapped across the genome and later augmented with an additional 4.6 million SNPs. Second, using population-wide correlations among the SNPs, the sequences of SNP sites on the reference genomes were segmented into a relatively small number of combinations of alleles, with the relatively consecutive linkage-disequilibrium blocks assumed to be separated by recombination hotspots. The combinations are referred to as haplotypes and the segments as haplotype blocks. (See, e.g., M. Stephens and P. Donelly, *A Comparison of Bayesian Methods for Haplotype Reconstruction from Population Genotype Data*, American Journal of Human Genetics, 73, 5, 1162-1169 (2003).

One deficiency associated with HapMap project based technologies, however, can be that subsequent analyses on the population can be carried out using these inferred blocks independently of any validity as to whether the individual actually physically carries such haplotypes in their genome. Further, a problematic circularity reasoning can be associated with this process because the population, which can be used for haplotype inference, can then be analyzed by the same haplotypes used to understand population stratification, disease association and selection processes acting on these genomes, for example.

Another significant problem with these technologies can be the assumption that all sequence variations in the human genome are single nucleotide mutations. Indeed, this assumption has been challenged by the serendipitous detection of CNPs through array comparative genome hybridization (array-CGH) technologies. Initially, copy-number fluctuations in the genomic segments likely were assumed to be a hallmark of cancer genomes, to arise by somatic mutations, and implicitly to be so detrimental to the normal genomes that they were not expected to vary in the germ-line genomes. However, the technology that likely revealed these polymorphisms and can currently be used to study these variations, such as array-CGH, can be incapable of characterizing their exact long-range structural properties involving, e.g., chromosomal inversions, translocations, segmental deletions, segmental duplications and large-scale aneuploidy), and can thus be of limited utility. Moreover, these CNVs may not be detected or be positionally and/or haplotypically located by using conventional short-range non-contextual shotgun sequencing technologies, for example. (See, e.g., L. Feuk et al., *Structural Variation in the Human Genome*, Nature Review Genetics, 7, 2, 85-97 (2006); and J. Sebat et al., *Large-Scale Copy Number Polymorphism in the Human Genome*, Science, 305, 5683, 525-528 (2004)).

Despite the difficulties described above, which can significantly undermine the reliability of population-wide genomic studies in the short term, researchers have focused on the algorithms for interpreting the data from high-throughput short non-contextual sequence reads from recently developed (next-generation) sequencing platforms. For example, it can be preferable for these sequence reads to either be assembled into contiguous overlapping sequences encompassing the information contained in each haploid chromosome, or be aligned to a phylogenetically reasonably close haplotypic reference sequence. A capture-recapture based statistical analysis of the databases of known SNP and CNV polymorphisms can indicate that about a few thousand haplotypic whole-genome reference sequences of properly sampled individuals from a human population can suffice, as indicated by, e.g., I. Ionita-Laza, currently unpublished results. However, such resources having a sufficiently large number of reference sequences are likely unavailable. Rather, databases of SNPs and CNVs and a very small number of reference genotypic sequences are in existence. Thus, the currently available bioinformatics procedures can be limited in that they can work with this available data to interpret only short-read sequence data, for example.

Further exacerbating the problem can be that when the sequencing technology provides only short non-contextual genotypic reads, as can be the case with heretofore available sequencing platforms, unambiguous interpretation of the polymorphism information can become computationally demanding. For example, as the reads become shorter and/or the base-calling algorithms introduce further errors, it can become increasingly difficult to align a sequence read to a single genomic region unambiguously. Thus, even when data can be available for reference sequences and SNPs with a population-based phasing into haplotype blocks (e.g., each block supporting a small number of haplotypes), because a proper interpretation of the resequenced data can involve enforcing certain parsimony constraints, such as interpreting with minimal number of haplotype blocks or minimal number of additional recombination sites. The resulting formulation can typically involve computationally hard non-convex combinatorial optimization. Thus, what can be counterintuitive, as the depth of the reads increases, without providing accurate overlap and contextual information, the underlying computational problems can become increasingly more intractable unless other helpful heuristics are utilized. For example, computational intractability, which can be inherent to these problems, can be ameliorated through exploitation of the underlying probabilistic structures of the data. Although such analysis as described below, can provide an indication about the nature of and parameters involved in certain probabilistic 0-1 laws that can guide the design of a preferred strategy for data collection using multiple platforms, it is possible that the optimal designs have to be ultimately discovered using real genomes through large-scale simulation tools, for example.

While it is likely believed that the algorithms and the software that can be used to support this approach can present a more meaningful interpretation and thus be of potential benefit and value with respect to genomic biomarker discovery and associated development cost, these types of solutions can most likely be short-lived. This is because, for example, as the sequencing technologies improve to provide long-range contextual information together with longer read lengths, it is possible that the problem of aligning reads uniquely can unlikely remain a significant issue. However, it is likely that new algorithmic problems will arise and have to be addressed ab initio which did not exist in the simpler platforms, such as how to efficiently align longer reads or maps, how to detect and interpret structural variations that can now appear rampant in the human genome, and how to handle new sources of statistical errors (e.g., false-positive and false-negatives in detecting markers such as restriction or hybridization sites).

Yet another challenge can be, e.g., with respect to developing technology-agnostic procedures, is the use of scalable and accurate procedures for sequences, maps and whole-genomes alignment, which can involve parallelism, genome-structure based heuristics and probabilistic methods. While such a problem can be solved via a branch-and-bound strategy, any such solution is not likely to determine an optimal (preferred) result in a polynomial-based amount of time in the worst-case, especially when each sequence-read can have a relatively large number of ambiguous alignments). Other approaches can involve seeking approximate solutions using linear programming relaxation heuristics or specific Bayesian statistical methods that can assume certain priors. For example, such approaches can be achieved through model-base analysis of the sequencing data (See, e.g., Erlich Y., et al., supra.). However, as described in this reference, there can exist in, e.g., a Solexa sequencing platform, nonstationary noise factors which can accumulate throughout a run and thus reduce yield and accuracy for subsequent sequencing cycles, as well as other associated problems as described herein.

For example, one dominant noise factor can be phasing, which can be a well-known source of noise in many sequencing-by-synthesis platforms which use a cyclic reversible termination (CRT) process. CRT can repeat cycles of three steps, e.g., (i) extension of a nascent strand with addition of a single extension-blocked fluorophore-labeled nucleotide, (ii) imaging and (iii) removal of the block and fluorophore in preparation for the next synthesis cycle. In an idealized model, the nascent strands within a clonal DNA cluster can all be the same and remain perfectly synchronized, thus generating a strong coherent signal. Imperfections in the chemistry of CRT, however, can cause stochastic failures which in turn can cause nucleotide misincorporations and imperfect (e.g., suboptimal, less than preferred) block removal in a particular cycle. The resulting heterogeneity in nascent strand lengths can manifest itself in lagging (behind the dominant nascent strands) and leading (ahead of the dominant nascent strands) members within the cluster, which can thus degrade the signal with sequence-specific noise from neighboring positions, for example. The noise introduced in this manner can be nonstationary and structured, as it can depend on, e.g., the number of preceding cycles and base-composition in the neighborhood of the interrogated location. Another dominant noise factor can be fading, which can be an exponential decay in fluorescent signal intensity that can increase with the number of preceding cycles. A resulting degradation of signal-to-noise ratio can typically be attributed to a material loss during sequencing, for example. Yet another dominant noise factor can be a cycle-dependent change in fluorophore cross-talk, which can induce a significant bias toward certain base calls in later cycles. Indeed, individually and/or together, these noise factors can have a significant negative effect on the quality of the signal that can be produced by the sequencing machine.

Certain approaches have been described in an attempt to address these problems, such as described in, e.g., Erlich Y. et al., supra., although these approaches can have several limitations. For example, one such limitation can be, e.g., that Alta-Cyclic technologies can be slow, with the majority of the computation spent on sparse-matrix manipulation. Another limitation can be, e.g., that Alta-Cyclic technologies can produce only one solution, e.g., the MLE solution. Yet another problem can be, e.g., that Alta-Cyclic technologies can lack flexibility. The Alta-Cyclic based implementations can have require to be repeatedly rebuilt to create new models, with new families of parameters and new estimation routines, every time the sequencing platform makes even a small modification to the underlying chemistry and physical sensing, for example. Yet still another problem can be, e.g., that Alta-Cyclic technologies can not generalize to a large class of sequencing platforms even though these parameters may share many of the same structures. Alta-cyclic and related technologies can be too inflexible to allow extension of the method from Solexa to 454, which may not have cyclic reversible termination and resulting homopolymer errors, although 454 can have its own phasing, fading and cross talk errors. Yet still another problem associated with Alta-Cyclic technologies can be, e.g., that such method can not provide for relatively easy integration with other higher-level modules, such as, e.g., alignment, SNP-calling, overlap detection, layout-generation, consensus sequence generation, shotgun, map-based assembly, etc.).

Thus, it may be beneficial to address and/or overcome at least some of the deficiencies described herein above.

SUMMARY OF EXEMPLARY EMBODIMENTS OF THE DISCLOSURE

Indeed, one of the objects of certain exemplary embodiments of the present disclosure can be to address the exemplary problems described herein above, and/or to overcome the exemplary deficiencies commonly associated with the prior art as, e.g., described herein. Accordingly, for example, provided and described herein are certain exemplary embodiments of exemplary methods, procedures, computer-accessible medium and systems according to the present disclosure which can be used for base calling and/or alignment.

According to one exemplary embodiment of the present disclosure, an exemplary computer-accessible medium can be provided that can have instructions thereon for base calling and/or alignment. When the instructions are executed by a hardware processing arrangement, the instructions can configure the hardware processing arrangement to obtain raw output from a sequencing platform that can be configured to be used for reading a fragment of at least one genome. The processing arrangement can be further configured to obtain a plurality of reference sequences for the at least one genome that can be obtained independently from the raw output obtained from the sequencing platform, and generate a base-call interpretation and/or alignment using the raw output and/or the plurality of reference sequences.

In certain exemplary embodiments according to the present disclosure, the processing arrangement can be further configured to determine a score function that can be based on information associated with the sequencing platform, and, using the score function, analyze polymorphisms based on the base-call interpretation and/or the alignment. The sequencing platform can be further configured to utilize a Sanger chemistry procedure, a sequencing-by-synthesis procedure, sequencing-by-hybridization procedure and/or a sequencing-by-ligation procedure. The raw output can include a plurality of randomly located short sequence reads, and at least one error associated with at least one of the randomly located short sequence reads. The error(s) can be related to an incorrect base-call, a missing base, an inserted base and/or a homopolymeric compression, for example.

The genome(s) can be and/or include a genome from one or more diseased cells, normal cells, individual organisms, populations, and/or ecological systems. Additionally, the reference sequences can be obtained from one or more diseased cells, normal cells, individual organisms, populations and/or ecological systems. It is also possible for the reference sequences to be obtained from a mathematical model, existing data, genomic single-molecules and/or genomic materials that can be amplified and/or otherwise modified. Further, according to certain exemplary embodiments of the present disclosure, the reference sequence(s) can be obtained from a reference haplotype, a genotype whole-genome sequence, a reference collection associated with a phased, unphased, haplotyped and/or genotyped sequence contig, a population-wide whole-genome sequence, and/or a population-wide collection of a phased, unphased, haplotyped and/or genotyped sequence-contig, for example. Further, the analyzing procedure can include a branch-and-bound process, for example.

According to another exemplary embodiment of the present disclosure, for example, an exemplary method and/or procedure can be provided for base calling and/or alignment, which can include, e.g., obtaining raw output from a sequencing platform that can be configured to be used for reading a fragment of at least one genome, obtaining a plurality of reference sequences for the at least one genome that can be obtained independently from the raw output, and, utilizing a hardware processing arrangement, generating a base-call interpretation and/or alignment using the raw output and/or the reference sequences. The exemplary method and/or procedure can further include determining a score function based on information associated with the sequencing platform(s), and, using the score function, analyzing polymorphisms based on the base-call interpretation and/or the alignment.

For example, the raw output can include a plurality of randomly located short sequence reads and error(s) that can be associated with the randomly located short sequence reads and related to an incorrect base-call, a missing base, an inserted base and/or a homopolymeric compression, for example. The exemplary method and/or procedure can further include the display and/or storage of information associated with the base-call interpretation and/or alignment in a storage arrangement in a user-accessible format and/or a user-readable format.

According to yet another exemplary embodiment of the present disclosure, for example, an exemplary system can be provided for base calling and/or alignment. The exemplary system can include, e.g., a computer-accessible medium having executable instructions thereon. When a computing arrangement executes the instructions, the computing arrangement can be configured to, e.g., obtain raw output from a sequencing platform configured to be used for reading a fragment of one or more genomes, obtain reference sequences for genome(s) independently from the raw output, and generate a base-call interpretation and/or alignment using the raw output and the plurality of reference sequences.

The exemplary computing arrangement can be further configured to determine a score function based on information associated with the sequencing platform, and using the score function, analyze polymorphisms based on the base-call interpretation and/or the alignment. The raw output can include randomly located short sequence reads, as well as one or more errors associated with the randomly located short sequence reads and related to an incorrect base-call, a missing base, an inserted base and/or a homopolymeric compression, for example.

These and other objects, features and advantages of the present disclosure will become apparent upon reading the following detailed description of exemplary embodiments of the present disclosure, when taken in conjunction with the accompanying exemplary drawings and appended claims.

BRIEF DESCRIPTION OF THE DRAWINGS

The foregoing and other objects of the present disclosure will be apparent upon consideration of the following detailed description, taken in conjunction with the accompanying exemplary drawings and claims showing illustrative embodiments of the invention, in which:

FIG. 2 is an illustration of exemplary base-caller pseudo computer code using an exemplary beam search strategy in accordance with certain exemplary embodiments of the present disclosure;

FIG. 5($a$) is an exemplary flow diagram illustrating a traditional resequencing procedure;

FIG. 5($b$) is an exemplary flow diagram illustrating an exemplary procedure in accordance with certain exemplary embodiments of the present disclosure;

FIG. 6($b$) is an illustration of graphs showing filtered intensity values corresponding to the intensity values of FIG. 6($a$) after being processed by an exemplary procedure in accordance with certain exemplary embodiments of the present disclosure;

Figure 1:
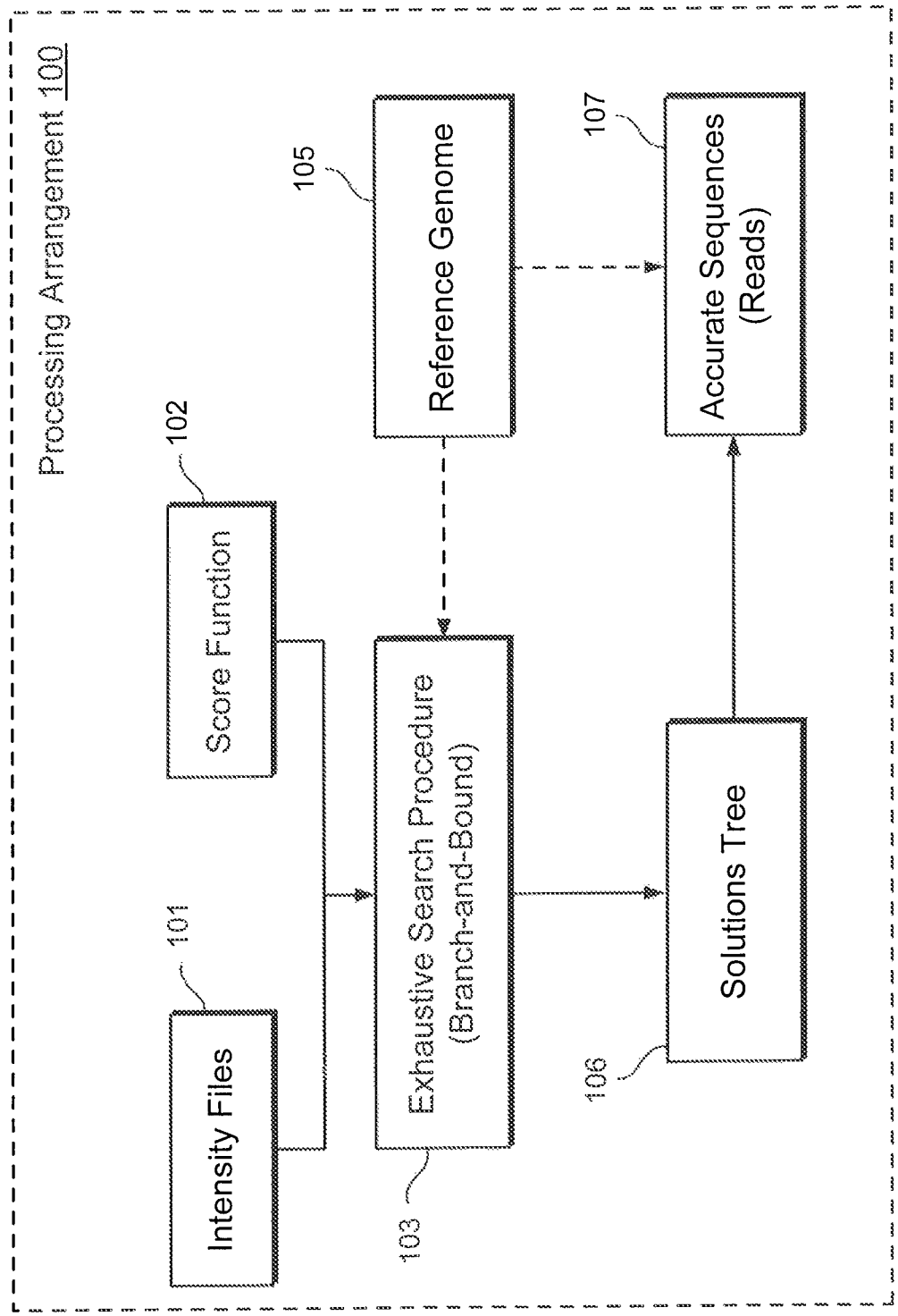
FIG. 1 is an exemplary flow diagram showing exemplary base-caller data flow in accordance with certain exemplary embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY
EMBODIMENTS OF DISCLOSURE

For example, exemplary embodiments in accordance with the present disclosure can address bioinformatics problems described herein above to be solved in order to handle the data from certain available sequencing technologies. Further, exemplary embodiments in accordance with the present disclosure can also be useful to anticipate potential future needs by creating a general probabilistic framework that can be helpful to provide an exemplary architecture of methods, procedures, computer-accessible medium and systems that can utilize data from future sequencing platforms In accordance with certain exemplary embodiments of the present disclosure, it is possible to address the issues described herein above by, e.g., providing exemplary rigorous common probabilistic frameworks, which (with parametric tailoring) can be applicable to various platforms, by formulating the structure of basic bioinformatics problem modules in terms of global optimization specifications, and by solving them using efficient statistical algorithms, whose computational complexity could be tamed through score-based branch-and-bound implementations. Exemplary embodiments in accordance with the present disclosure can indicate how to avoid dependence on greedy heuristics that myopically trade-off global optimality for computational efficiency.

Certain exemplary embodiments according to the present disclosure can be used to determine and utilize a probabilistic extension and alignment of ultra-short (e.g., 30-60 bps) sequence-read data, which data can be deficient due to, e.g., a loss of synchronization in addition to other deficiencies described herein. Such data can be associated with certain available and/or anticipated sequencing technologies (e.g., Solexa, etc.), whereas such class of technology can be referred to as "Short Read Sequence Extension and Alignment".

For example, according to certain exemplary embodiments of the present disclosure, parametric and/or non-parametric score function(s) can be used in a branch-and-bound-based exhaustive search approach to efficiently solve various non-convex optimization problems appearing in the exemplary procedures used to solve base-calling for a wide class of DNA sequencing platforms, align the raw reads directly to any given DNA sequence (e.g., a reference sequence), and use the data to detect (directly or indirectly) a wide class of polymorphisms (e.g., SNPs, CNVs, indels, SVs, etc.) Accordingly, certain exemplary methods, computer-accessible medium, and systems are described herein for base-calling, resequencing, aligning, polymorphism detection, etc. using data obtained directly from various sequencing platforms, known haplotypic or genotypic reference sequences and databases of polymorphisms. These exemplary methods, procedures, computer-accessible medium, and systems can provide important strategies that may be used for statistically combining disparate genomic information, and exemplary embodiments of chemical protocols can be utilized which may, e.g., in parallel, manipulate and interrogate a large amount of genomic, sequencing, polymorphism, and disease association data in various environments (e.g., personalized medicine, population studies, clinical studies, pharmacogenomics, etc.).

In addition, exemplary embodiments of methods, procedures, computer-accessible medium, and systems for base-calling, alignment, and polymorphism detection are provided herein. Certain exemplary applications of such exemplary methods, procedures, computer-accessible medium and systems according to the present disclosure can include, e.g., analyzing patient genomes to predict susceptibility to various genetic or genomic diseases, or analyzing patient genomes to diagnose genomic instability and mutations as the basis of cancer. Exemplary embodiments according to the present disclosure can also have agricultural and/or biomedical applications in drug and/or vaccine discovery and applications, through understanding the behavior of a cell in an altered state (e.g., cancer, neuron-degeneration, auto-immune disease, etc.) genetically modifying a natural wildtype organism, genetic engineering, etc. Exemplary applications also can include, e.g., understanding population dynamics, neural behavior, evolutionary processes, genome evolution and aging, for example.

Also described herein are exemplary embodiments of methods, procedures, computer-accessible medium, and systems according to the present disclosure that can comprise and/or be configured to obtain raw output that can include short-sequence reads from one or more sequencing platforms, while the choice of platform(s) to be selected can be based on user-preference and/or other criteria. It is possible to obtain one or more reference sequences, and interpret the raw-output data and align the short sequences to reference sequence(s), which can be performed in one integrated subprocess or in two separate subprocesses, to detect various polymorphisms.

Using certain exemplary embodiments in accordance with the present disclosure, it can be possible to compute or determine one or more of most plausible solution(s) by searching the hypotheses space with a score function, which can be built out of (e.g., computed, processed, calculated, determined, derived, etc.) a log-likelihood function (e.g., from a parameterized model as done earlier). According to certain exemplary embodiments of the present disclosure, exemplary penalty (and/or score) function(s) can be determined and/or used that can relatively quickly recognize hypotheses that would unlikely be as true. For example, an exemplary good (e.g., preferred) penalty and/or score function of this nature can include read-length-dependent upper and lower bounds determined so that unlikely solutions can be readily identified as they are scored (with a relatively very high probability) outside of the ranges defined.

It is possible to perform global optimization (or near optimization) by searching the hypotheses space potentially exhaustively (or near exhaustively) utilizing an intelligent pruning procedure using exemplary branch-and-bound heuristics. For example, the search tree can be a pruned quaternary tree (e.g., branching factor=4), where each node in position j can be expanded to the (j+1) position by augmenting the path with the base A, T, C, and G, and scoring a new resulting path for the hypothesis that it could have generated the data, which, in reality, can be obtained from the sequencing platform. If the score for a new node is below the desired range, the node can be pruned. In a more aggressive approach, it can be possible to utilize an exemplary embodiment using beam-search heuristics, where at any point only a fixed number (e.g., k=20) of the best possible hypotheses can be allowed to survive pruning and be included.

With a good (preferred) exemplary parameterized model and the ability to compute an exemplary score analytically, the pruning procedure can be further simplified. For example, if the score function is linear and/or obeys the principle of optimality, it is possible to use exemplary tools such as those described by dynamic programming procedures. For certain score functions which can have a stringent local structure, the exemplary procedure can be implemented in such a way that it can utilize a greedy algorithm, dynamic programming algorithm and/or graph search algorithm.

In addition, certain exemplary embodiments according to the present disclosure can provide a situation where it may not be possible to have a score function with preferred qualities and/or characteristics, or to derive such exemplary qualities from an understanding of the underlying physical and chemical processes (e.g., the polymerase chemistry can be highly base-specific or lead to stuttering in a way that can not be fully understood). In such cases, it is possible to generate a non-parametric model according to certain exemplary embodiments of the present disclosure where a database containing a large number of observed base-calling of known sequence reads can be used to model the likelihood that a given hypothetical sequence of bases could have generated a particular data set, and thus to generate an exemplary score (and/or penalty) function, such as of the kind described hereinabove, for example. Such exemplary approach (procedure, method, technique, etc.) can be used to generate an exemplary tree with paths that can provide many plausible hypothetical solutions, which can be sorted by the exemplary score values, for example.

The members of an exemplary ordered collection of solutions, as can be produced by exemplary embodiments in accordance with the present disclosure, can be further assigned an exemplary empirical p-value and used to, e.g., control false discovery rates. The generality and/or flexibility of an exemplary procedure in accordance with the present disclosure can be derived from its formulation of the problem in terms of global optimization, and its relatively efficient implementation using an exemplary branch-and-bound process. As the technology platform changes, exemplary embodiments in accordance with the present disclosure can be adapted to the newer platform or change to another platform by modifying the score function and/or by searching over different databases, for example.

Another advantage of certain exemplary embodiments according to the present disclosure can be with respect to how they can be integrated (e.g., interfaced, connected, etc.) with higher-level procedures and/or processes. For example, the problem of directly aligning a read from a sequencing platform (e.g., Solexa) with a particular segment of an organism's putative reference genome can be described as follows. While traditionally, the problem can be attempted to be solved by first executing a base-calling routine (e.g., Alta-Cyclic) on the data, and then using the output of this routine to perform a sequence alignment (e.g., BLAST, Smith-Waterman, SWAT, Neelerman-Wunsch, NEEDLE, etc.), according to certain exemplary embodiments of the present disclosure, an exemplary tree-search with branch-bound procedure can be used that can combine two or more factors in its score. For example, one factor can represent how good of a match there is to the genomic segment (e.g., the edit-distance from the genomic segment). Another factor can represent how likely it is to have generated the observed data.

Exemplary embodiments according to the present disclosure can be implemented in terms of (a) hexanary trees with branching for 6 possibilities, e.g., match-A, match-T, match-C, match-G, insert-nucleotide and delete-nucleotide, and (b) evaluation with respect to an edit transcript as opposed to a sequence. Additional generalizations respecting other higher level algorithmic problems can include, e.g., SNP-calling, overlap detection, layout-generation, consensus sequence generation, shotgun or map-based assembly, as one having ordinary skill in the art should appreciate in light of the teachings provided herein.

Based on these general schemes, exemplary embodiments in accordance with the present disclosure can also adapt these such procedures to SNP calling and CNV detection.

For the SNP calling, certain exemplary embodiments according to the present disclosure can be used to extend the length of the sequence reads by running the base-calling routine for longer read lengths and keeping track of many plausible solutions with each base of the output reads (as well as the whole read) which can be scored as described herein above, for example. Since exemplary embodiments according to the present disclosure can obtain multiple alignments with appropriate base-calling and base-scoring, it is possible to convert the data into a SNP-calling score that can evaluate any particular base to be a single-nucleotide polymorphism, for example. By using an empirical-Bayes method for false-discovery rate control (see, e.g., Efron, B., *Large-scale simultaneous hypothesis testing: the choice of a null hypothesis*, J. Am. Statist. Assoc., 99, 96-104 (2004)), exemplary embodiments according to the present disclosure can generate an empirical null model, which can distinguish true SNPs from false-positive ones. By further combining such data with the available HAPMAP database, it is possible to further distinguish detection of already known SNPS from novel SNPS.

One having ordinary skill in the art will appreciate in light of the teachings described herein various other benefits of exemplary embodiments of the present disclosure in areas of intelligent experimental design. For example, such benefits can be especially useful in a design a SNP calling algorithm that can combine unequal coverage of reads from multiple platforms, e.g., shallow coverage of 454 sequence reads with a deeper coverage Solexa reads. In one such example, it is possible to determine that the 454 sequence reads have a longer length (e.g., about 700 bps to about 1000 bps), although can not always be ideal or preferred for detection of novel SNPs because its homo-polymer errors can obfuscate the data. Nonetheless, these exemplary reads can provide a better indication of which SNPs of a particular haplotype from a haplotype block are being selected, and thus can help in resolving the multiple alignment problems for Solexa reads. However, by selecting the coverages for each kind of reads, base-calling parameters, read lengths, etc. it is possible to achieve designs best (or/and preferably) suited for accurate (or reasonably accurate, sufficiently accurate, etc.) SNP detection. While it is possible for a rough approximation of these parameters to be calculated analytically using probabilistic analysis, exemplary embodiments in accordance with the present disclosure can select the most optimal values utilizing a large-scale genomic simulation that can use, e.g., realistic models of genomes, populations, population structure, the score function(s) used by the algorithm(s) and the error model(s) for the sequencing platform(s).

Exemplary embodiments in accordance with the present disclosure can address the CNV detection problem by, e.g., building on the exemplary alignment algorithm and/or procedure module in a manner similarly to as described herein with respect to the SNP calling problem. However, structural variations can introduce breakpoints in a sequence read that possibly do not appear in the reference sequence. Thus, an exemplary alignment procedure in accordance with the present disclosure can search over the appropriate suffixes and prefixes. For this purpose, it is possible to break the reads into a set of k-mers, which it can first use to detect their rough alignment to the genomes using, e.g., preprocessing and efficient data-structures such as suffix arrays, suffix trees or Burrows-Wheeler indexing, and others as one having ordinary skill in the art should appreciate in view of the teachings provided herein. However, when the coverage is low, the statistical significance of copy-number estimation can become an important issue.

For example, this exemplary problem can be addressed by certain exemplary embodiments in accordance with the present disclosure using a suitable (preferred) choice of the parameters in experimental design, which can likely involve a hybrid technique and/or procedure that can involve shallow-coverage data of long reads (e.g., 454-instrument). This can facilitate a detection of the break-points and deep-coverage data of short reads (e.g., Solexa platform), which can help achieve a better estimation of copy number. This exemplary analysis can be further coupled to a low resolution CNV analysis with a local copy-number segmentation algorithm. It can be assumed that the low resolution data can have been obtained using a low-complexity representation of the genome, which can be sequenced with short reads. Other variations, which one having ordinary skill in the art should appreciate in view of the teachings provided herein, can be handled with appropriate changes to the basic procedures. For example, in accordance with certain exemplary embodiments according to the present disclosure, the data from different sources (e.g., low-resolution segmentation, high resolution deep-coverage short reads, high resolution low-coverage short reads, etc.) can be algorithmically combined to obtain a relatively accurate copy number estimation. Similarly to the SNP data, it can be possible that the most optimal design (e.g., implementation) can be achieved through a large-scale simulation.

As discussed herein, advances in genomic related technologies, such as the development of recent sequencing technologies, have likely created further opportunities for interpreting data from recent (e.g., next generation) sequencing platforms using a general probabilistic framework. The resulting interpretations can have various biomedical applications, such as, e.g., finding common variants in polymorphisms, performing association studies, identifying certain genes that can be commonly implicated in diseases, and elucidating many of the cellular pathways upon which they act. Certain exemplary embodiments according to the present disclosure can provide relatively robust, efficient, and inexpensive technologies that can be used for, e.g., base-calling, resequencing, sequence alignment and detection of polymorphisms. For example, exemplary embodiments of methods, procedures, computer-accessible medium and systems can be provided for, e.g., base-calling, alignment and polymorphism detection.

In comparison to conventional technologies which can utilize greedy (e.g., relatively complex) heuristics and/or idealized model based simplification with suboptimal accuracy, certain exemplary embodiments in accordance with the present disclosure can be provided which use a global search-method with branch-and-bound heuristics (or beam search) to contain the complexity to relatively lower levels. Further, certain exemplary embodiments in accordance with the present disclosure can be used to determine a globally optimal solution and thus achieve a relatively high level of accuracy. In order to achieve a high computational space and time efficiency, certain exemplary embodiments according to the present disclosure can, e.g., prune out branches and utilize a selected score function.

For example, accuracy and validity of base-calling (and subsequent and/or integrated applications) can depend upon the fidelity of the underlying models describing the "error processes" that can be involved in the generation of raw data from a sequencing platform and reflected in the score. An exemplary score function can combine a Bayesian likelihood obtained from prior distributions derived from an exemplary model and certain penalty functions corresponding to certain constrains.

Relatively simple but meaningful heuristic score functions and/or penalty functions can be utilized according to certain exemplary embodiments of the present disclosure. For example, such exemplary functions can be provided by a human expert, and/or learned from (e.g., based upon, derived from, etc.) data utilizing a known "machine learning" approach, and/or by empirical Bayes approaches that can derive priors directly from the data. It is possible to utilize an empirical-Bayes method to determine the statistics and thresholds (e.g., null-model, threshold, p-values, base- or sequence-quality), thereby making the system relatively independent to the underlying technology, while being able to mix-and-match certain technologies, for example. In addition to the score functions, based on certain modeled, learned or known models, it is possible to use any other additional information (e.g., reference sequence or polymorphism databases, etc.), which can sharpen the exemplary score function and make the exemplary algorithm behave more efficiently.

Further, certain exemplary procedures according to the present disclosure can utilize different/varying technologies including those for which no known models of error processes exist. For example, there can be available two different kinds of sequence-reads with two different length parameters from two different technologies that can be subjected to two different classes of error processes. From the data itself, it is possible to create an exemplary empirical model based on their interactions, and then use the resulting statistical distributions in the score function.

Additionally, certain exemplary embodiments of the procedures according to the present disclosure can be tuned heuristically (e.g., size of a priority queue and/or width of the beam search used in the branch-and-bound) to obtain the best (preferred, optimal, etc.) computational complexity and resource consumptions as a function of specific error parameters and preferred accuracy. Such exemplary processes can automatically provide a way to utilize underlying 0-1 laws in these technologies, such as, e.g., a law that states that there can exist certain error parameter thresholds (for which error processes that the underlying platforms' chemistry is subject) below which the probability of obtaining all the alignments correctly can be close to zero, while above this threshold, the correct alignment probabilities can jump (e.g., rapidly/sharply increase) to one. Such laws can have significant implications for the design of the underlying and/or applications, choice of the component technologies, parameters used in the technologies, and/or in selecting the manner in which the exemplary procedure can explore the search space which can be vast.

Moreover, according to certain exemplary embodiments of the present disclosure, the exemplary procedure can parallelize in a relatively straight-forward manner. Multiple regions can be explored simultaneously by different processors, with search trees starting with a small number of randomly selected initial seeds (e.g., sequence-reads from which a local assembly can be initiated).

For example, an exemplary embodiment of the procedure according to the present disclosure for base calling can be described relatively simply in terms of the following exemplary subprocesses (utilizing generalizations that should be apparent to one having ordinary skill in the art in light of the present disclosure):

a: Start with a single nucleotide base (e.g., A, T, C, G), which can be the root of an exemplary tree); and b: Generate a QUATERNARY Tree by, e.g., starting with an unexplored leaf node (labeled by a nucleotide base) with the best score-value, selecting all four possible nucleotide bases (e.g., A, T, C, G) to expand the node by making them its children and computing their scores, and repeating until the tree cannot be expanded any further.

The exemplary score function (and/or components thereof) can be built from (e.g., generated, derived from, based upon, etc.) the logarithm of intensity information from each base-read and its variance-based weighting of squared deviations computed using a distribution of similar positional intensities stored in an exemplary database. The exemplary database can be generated from a set of calibrating examples, which can be learned using machine-learning techniques and/or from a parametric model. It is also possible for the set to be adaptively and/or repeatedly learned and/or updated from each successive application of the exemplary procedure.

Further, certain exemplary embodiments of a base-calling procedure according to the present disclosure can use a relatively simple score function, its relative performance and relative accuracy with respect to the score functions that can be obtained by vendor-provided software. Such exemplary embodiments according to the present disclosure can utilize data obtained from Solexa reads of the viral genome from phiX, e.g., a bacteriophage.

For example, certain exemplary procedures according to the present disclosure can be implemented as a set of modular components that can be hierarchically combined and built upon the facilities available in a modular open-source assembler (AMOS), which was developed by a consortium of institutions and research centers associated with the University of Maryland. To facilitate the interaction of various isolated components, AMOS can facilitate a central data repository where certain genomic objects (e.g., reads, inserts, overlaps, contigs, scaffolds, etc) can be collected and indexed. Exemplary embodiments according to the present disclosure can extend such bank implementation to also provide for the storage of raw data from different sequencing platforms as well as whole genome reference sequences. Programs in the assembly pipeline can be suitably adapted to communicate among the modules using the exemplary bank as an intermediate storage space. Further, certain exemplary embodiments of the procedure according to the present disclosure can use an AMOS visual analytics tool (e.g., Hawkeye) for inspection and validation of the corresponding results, for example.

Further, certain exemplary embodiments in accordance with the present disclosure can address some of the problems and issues described above by ensuring that the underlying algorithms scale to other hardware platforms (e.g., cluster computers, multi-core architecture, cloud computing, etc.), and software architecture (e.g., MPI architecture, its successors and related designs).

For example, it is possible to consider nature of the genome alignment problems as follows. First, it is possible to consider sequencing the genome of an individual at a reasonable coverage with sequencing platform, e.g., Solexa machine, providing about a hundred million reads each of length about 50, which reads can be referred to as $r_1$, $r_2$, ... $r_k$. Further, it is possible to assume that an arbitrary read, say $r_i$, can align to several chromosomal locations in a genotypic reference sequence. Each such alignment can then be interpreted as implying that the read ri can belong to certain haplotype blocks, e.g., $h_j$, which can be assumed to have already been characterized from an existing population study of SNPs. It is also possible to denote such an event by a 0-1 variable $A(r_i, h_j)=1$, For example, the information connecting the reads to the haplotype blocks can be represented by a 0-1 integer matrix, A, with the conditions that $A(r_i, h_j)=0$ or 1. A certain independent 0-1 variable $x_j=0$ or 1 can exist, such that Ax=1 (e.g., for all i, sum_over_j $A(r_i, h_j) x_j=1$) can be satisfied. It is possible to obtain a solution that can minimize the total number of independent variables $x_j$ that can assume the value of 1 (e.g., min sum_over_j $x_j$). Such formulation can yield an Integer Linear Programming (ILP) problem, which in the general setting can be NP-complete and hence, for all practical purposes, intractable.

Certain exemplary embodiments of the present disclosure can improve the base-calling procedure for the sequencing platform, e.g., Solexa or other platforms, and thus extend the sequence read-lengths to be above a predetermined threshold value, e.g. about 100 bps (with some base-calls being inferred probabilistically with the estimated probability of the call recorded) so that the longer sequence-reads can be aligned almost uniquely, which can thus simplify the combinatorial optimization problem, for example. It is also possible to utilize certain potentially more-beneficial design strategies that can distribute tasks to more than one sequencing and mapping platform as well as to those that can combine sequence alignment and base calling in a single unified exemplary framework.

For example, in considering a sequencing platform that can produce short-reads of length k (in an idealized case with no base-call and/or homopolymer errors for explanatory purposes), such short-reads can then be aligned to an idealized random genome of length G. It can be assumed that all of the sequence-reads together cover the genome by a coverage factor of c. Accordingly, the probability that all of the sequence reads have unique locational identities and that the alignment algorithm can find all of them can be expressed as $\exp[-cG^2/(k4^k)]$. Thus, for a fixed genome, whose length is G, if the read length is smaller than a threshold of $[1/(\ln 4)][2 \ln G+\ln c+\ln(1/eps)]$, the probability can take a relatively small value (e.g., be relatively closer to 0).

Further, as this threshold is exceeded, the probability can sharply rise to a value that can be very close to 1 (e.g., 1−eps) and the exemplary procedure can become computationally tractable, although it still can involve utilizing certain pre-processing and data-structures such as suffix trees and Burrows-Wheeler indexing to devise acceptable heuristics. It is possible to utilize such 0-1 laws (e.g., computational phase transition) in certain biological implementations and applications to circumvent the intractable computational complexity, which can be a significant technique used in matching particular genomic applications to the least expensive available biotechnology, for example.

Additionally, certain exemplary embodiments of a procedure according to the present disclosure can be based on a succinct parametric model that can address the dominant noise factors described herein above.

For example, it is possible that the base-calling problem can be reduced to, e.g., finding the most plausible hypothesis regarding the structure of a DNA sequence that can generate a particular data set being analyzed. If the underlying parameters of the model are known, then it is possible to describe the resulting likelihood (or log-likelihood) function that would score a hypothesized sequence as to its likelihood of generating a particular dataset. Thus, the computational function can then be to discover the most likely hypothesis quickly from an exponentially large search space, for example. For this particular problem formulation, the exemplary stochastic process can involve exponential distributions that can be governed by a relatively small number of parameters, e.g., lead, lag, fading, and cross-talk, which can be estimated using certain exemplary robust machine-learning algorithms. There can be a maximum likelihood estimation (MLE) formulation that can be solved using simplifying tools from linear-algebra which can optimize a score based on log-likelihood, for example. Thus, this estimation problem can have a reasonably efficient solution. This exemplary method and/or procedure can be implemented in the Alta-Cyclic system for Solexa base-calling. Such exemplary implementation can be effective and validate the exemplary model and the linear-algebraic formulation in terms of the log-likelihood score. For example, it is possible to extend accurate base-calls over read lengths of about 48 bps to about 78 bps, while producing mean error rates in SNP sites below about two percent.

It is also possible to use a random walk model which can be characterized by three parameters, e.g., block-removal probability, nucleotide misincorporation probability and template loss probability. When used in conjunction with a cross-talk matrix, it is possible to describe signal-distortion as a function of cycle. Thus, given a hypothesized DNA sequence of any length, the exemplary model can estimate the probability that a particular data set can be generated from such particular sequence.

To address some of the prior limitations described herein, certain exemplary embodiments in accordance with the present disclosure can prune most of the unnecessary computation in the early processing stages, and thus be able to operate faster when augmented with "smart" score-functions. For example, certain procedures in accordance with the exemplary embodiments of the present disclosure can be used to generate the best, second best, third best solution, etc. up to a desired bound, which can then be used to calculate p-values, generate a more robust maximum a posteriori (MAP) estimator, use Empirical-Bayes methods to create an empirical null model, control the false discovery rate, etc. Additionally, according to certain exemplary embodiments of the present disclosure, it is possible to circumvent some of the problems described herein above using exemplary non-parametric models, for example. Further, exemplary embodiments according to the present disclosure can integrate the higher level needs through a relatively simple modification to the score function, for example. Moreover, as one having ordinary skill in the art will appreciate in view of the teachings described herein, it is possible that many of the problems associated with heretofore available technologies do not exist.

FIG. 1 shows a flow diagram of an exemplary procedure for generating at least one nucleotide sequence in accordance with certain exemplary embodiments of the present disclosure. The exemplary flow chart illustrated in FIG. 1 illustrates a base-caller data flow according to certain exemplary embodiments of the present disclosure.

For example, as illustrated in FIG. 1, with the use of a processing arrangement (or computing arrangement) 100, exemplary intensity files 101 can be combined with an exemplary score function 102 and input into an exemplary exhaustive search procedure/process 103, which can be and/or include a branch-and-bound process in accordance with certain exemplary embodiments of the present disclosure. Input from a reference genome 105 can be used in the exemplary exhaustive search procedure/process 103. Output from the exemplary exhaustive search procedure/process 103 can be provided to an exemplary solutions tree 106. In accordance with certain exemplary embodiments of the present disclosure, accurate sequences (reads) 107 can be achieved (e.g., performed utilizing the processing arrangement 101) using information from the exemplary solutions tree 106. As further illustrated in FIG. 1, it is possible to also use input from the reference genome 105 to achieve and/or perform exemplary accurate sequences (or reads) 107 in accordance with certain exemplary embodiments of the present disclosure.

FIG. 2 shows an illustration of exemplary base-caller pseudo computer code using an exemplary beam search strategy in accordance with certain exemplary embodiments of the present disclosure. As illustrated in FIG. 2, exemplary base-caller pseudo computer code 200 can use as input start base $R_0$ 201 and max queue size K 202. As shown in FIG. 2, it is possible to start with a null set of leaves $T$ 203=0, and a set of live nodes $\mathcal{L}$ 204. The set of live nodes $\mathcal{L}$ 204 can include nodes queued in a first in, first out (FIFO) basis, such that $\mathcal{L}:=\{(R_0 \cdot g(R_0))\}$. While the set $\mathcal{L}$ 204 of live nodes is not empty (e.g., $\mathcal{L}$ 204≠0), the exemplary procedure, as implemented by the exemplary base-caller pseudo computer code 200, can sort the set of live nodes $\mathcal{L}$ 204 based on the their relative score. This exemplary procedure can then prune the queue to size K 202.

As further shown in FIG. 2, a base $R_i$ 205 can be expanded to generate $R_A \cdot R_T \cdot R_G \cdot R_C$. The exemplary code 200 can then determine whether each resulting base is a leaf. If so, the exemplary computer code 200 can add such to the set of leaves $T$ 203. If not, the node can be added to the queue. This exemplary procedure can be repeated until the set of live nodes $\mathcal{L}$ 204 is equal to zero, upon which an accurate sequence read can be provided/outputted (e.g., displayed and/or stored in a user-accessible format and/or a user-readable format). According to certain exemplary embodiments of the present disclosure, the exemplary computer code 200 can be implemented using a processing/computing arrangement, such as an exemplary processing arrangement 100 of FIG. 1.

Figure 3:
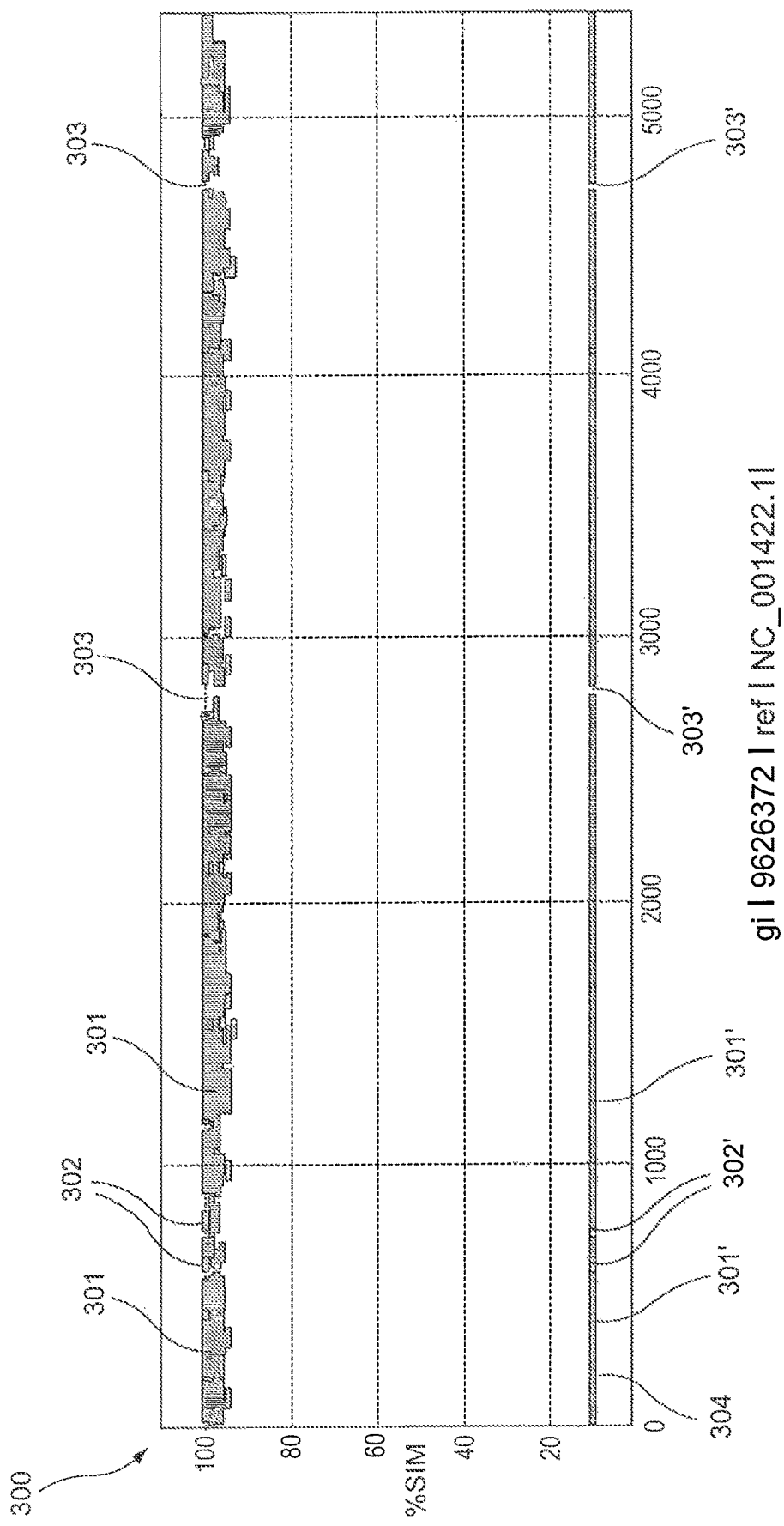
FIG. 3 is a graph of an exemplary percent identity plot in accordance with certain exemplary embodiments of the present disclosure.

FIG. 3 shows an exemplary percent identity plot in accordance with certain exemplary embodiments of the present disclosure. As shown in FIG. 3, an exemplary alignment of about 140,000 base-called sequences (reads) of about 78 bases to the phiX reference genome can be depicted. Forward matches 301 can be displayed with reverse matches 302. There are a relatively small number of gaps 303, e.g., in which there are no matches. A corresponding line 304 clearly indicates where there is predominantly forward matches 301, reverse matches 302 and gaps 303, as represented by indications 301', 302' and 303', respectively.

Figure 4:
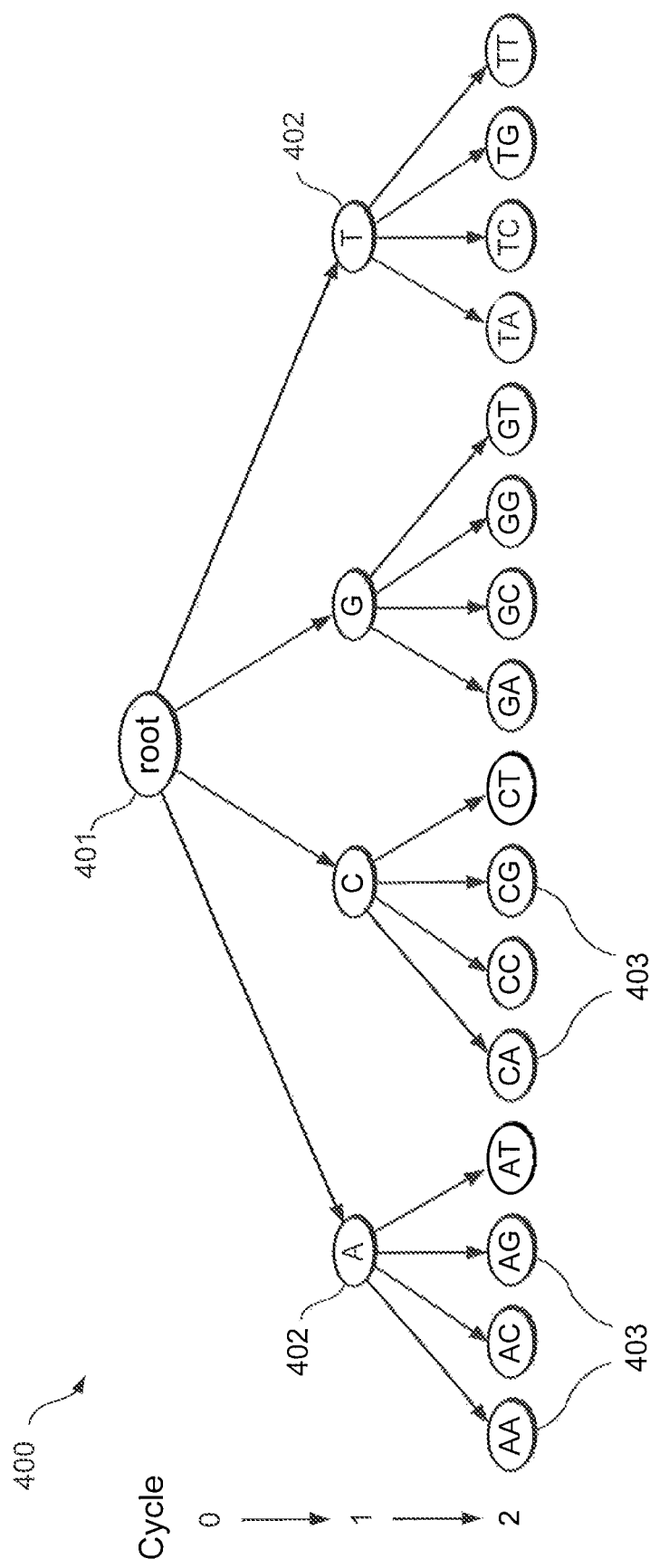
FIG. 4 is a diagram of an exemplary tree that can be generated by an exemplary base-caller procedure in accordance with certain exemplary embodiments of the present disclosure.

FIG. 4 shows a diagram of an exemplary tree that can be generated by an exemplary base-caller procedure in accordance with certain exemplary embodiments of the present disclosure. As shown in FIG. 4, an exemplary tree 400 can include root 401 corresponding to cycle 0. The tree 400 can be a quaternary tree (e.g., branching factor=4), where, at each cycle, each node can be expanded by 4, corresponding to A, T, C, and G, for example. Accordingly, in cycle 1, the root 401 can be expanded into four nodes 402. Similarly, in cycle 2, each of the four nodes 402 can be expanded into four nodes 403, resulting in a total of sixteen nodes 403 in cycle 2. The tree 400 can be further expanded in a similar manner in accordance with certain exemplary embodiments of the present disclosure. Further, the tree 400 can be used in, e.g., an exemplary branch-and-bound process, being pruned in accordance with certain exemplary embodiments of the present disclosure, such as shown in FIG. 2 and described herein. For example, it is possible to select all four possible nucleotide bases (e.g., A, T, C, G) of an unexplored leaf node with the best score-value to expand the node by making them its children, computing their respective scores, and repeat the process until the tree 400 cannot be expanded any further.

FIG. 5(a) shows an exemplary flow diagram 500 illustrating a traditional resequencing procedure. As shown in FIG. 5(a), intensities 501 can be input into a base caller traditional platform 502. The resulting values can then be processed by a sequence aligner 503 to generate output 504.

FIG. 5(b), in contrast, shows an exemplary flow diagram 510 illustrating a procedure in accordance with certain exemplary embodiments of the present disclosure. As shown in FIG. 5(b), intensities 511 can be input into an exemplary base-caller 512. The resulting values can then be processed by a sequence an exemplary aligner 513. In contrast to the traditional procedure illustrated in FIG. 5(a), the exemplary procedure shown in FIG. 5(b) can include an exemplary recycle loop 514 to repeat the process, and further refine the values until, e.g., a predetermined threshold level is met, a preferred level of accuracy is achieved, etc., before generating an output 515.

Figure 6A:
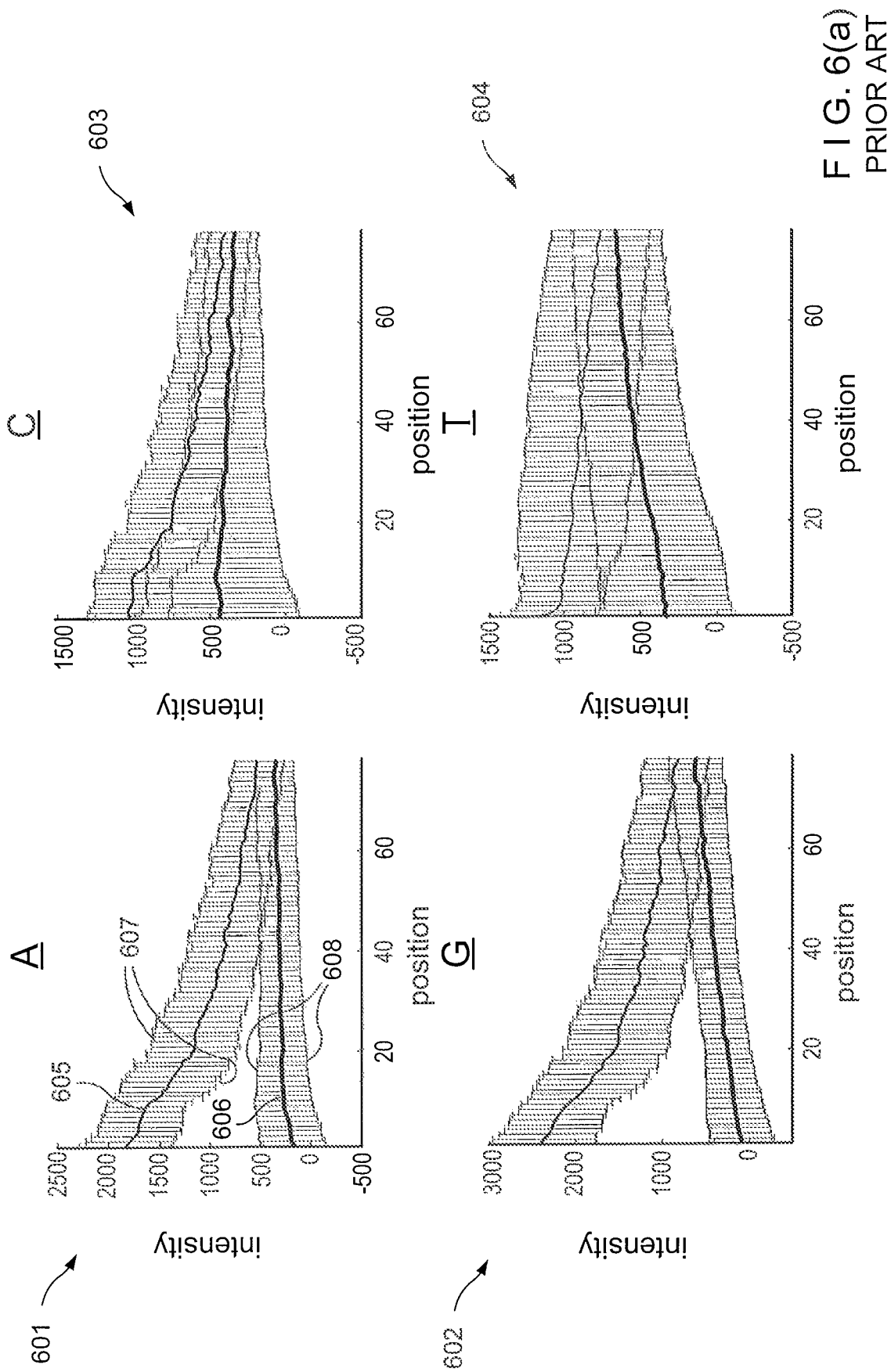
FIG. 6($a$) is an illustration of graphs showing raw intensity values generated by an Illumina technology.

FIG. 6(a) shows an illustration of graphs 601-604 corresponding to nucleotide bases A, C, G, T, respectively, showing raw intensity values generated by an Illumina technology. As shown in FIG. 6(a) by the labels for mean-averages 605, 606 and corresponding standard deviations 607, 608 of the signals generated by the Illumina technology for each channel, there can be a significant amount of noise associated with the signals associated with these raw intensity values. As described herein above, other previously known technologies likely also generate signals with similar or greater noise levels.

Figure 6B:
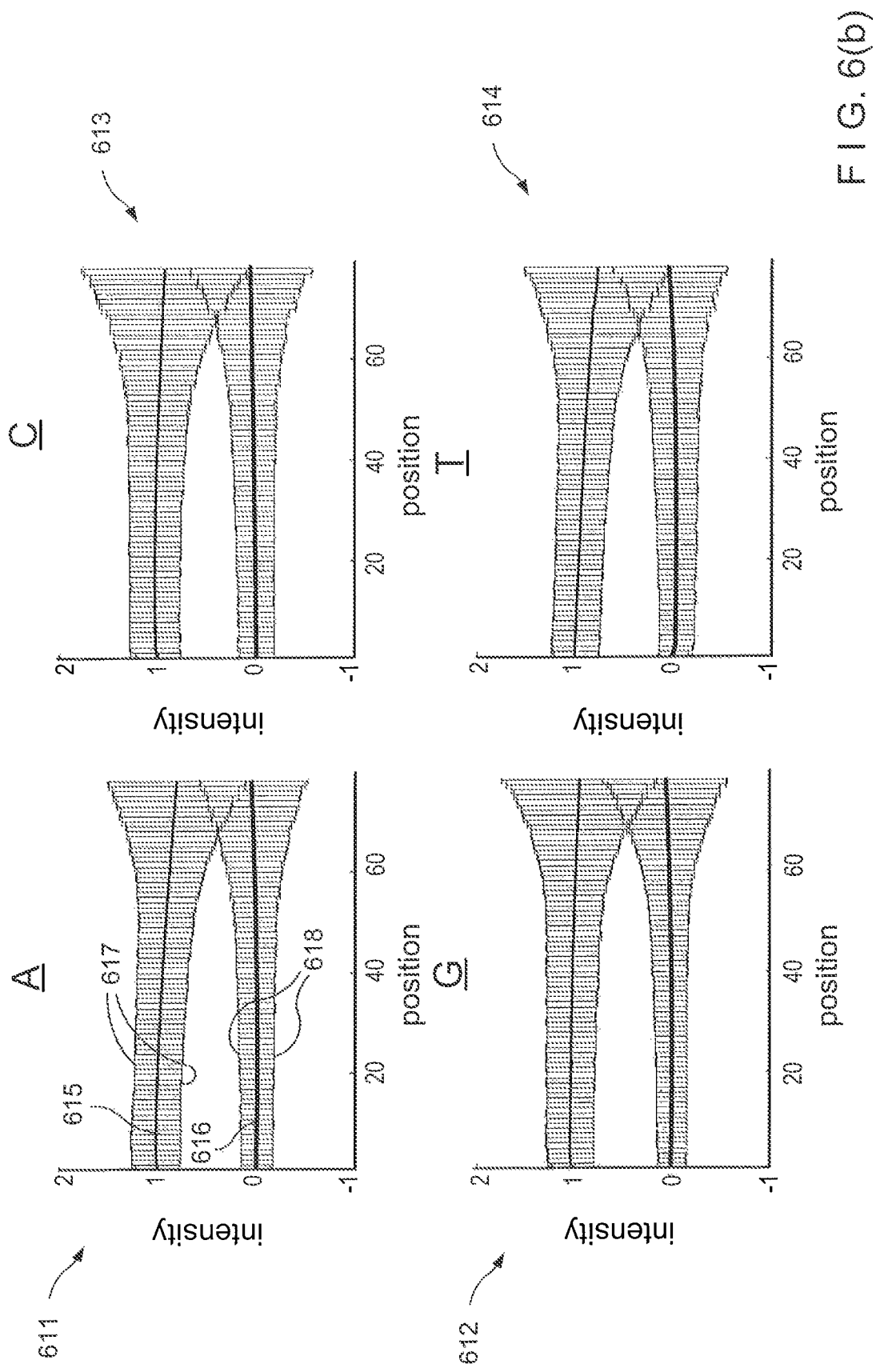

In contrast, FIG. 6(b) shows an illustration of graphs 611-614 corresponding to nucleotide bases A, C, G, T, respectively, illustrating filtered intensity values corresponding to the intensity values of FIG. 6(a) after being processed by an exemplary procedure in accordance with certain exemplary embodiments of the present disclosure. As shown in FIG. 6(b) by the labels for mean-averages 615, 616 and corresponding standard deviations 617, 618, the noise associated with the signals can be reduced using certain exemplary procedures according to the present disclosure described herein (e.g., by the exemplary procedure shown in FIG. 5(b) and described herein). For example, noise associated with crosstalk and lagging can be reduced by certain exemplary embodiments according to the present disclosure.

Figure 7:
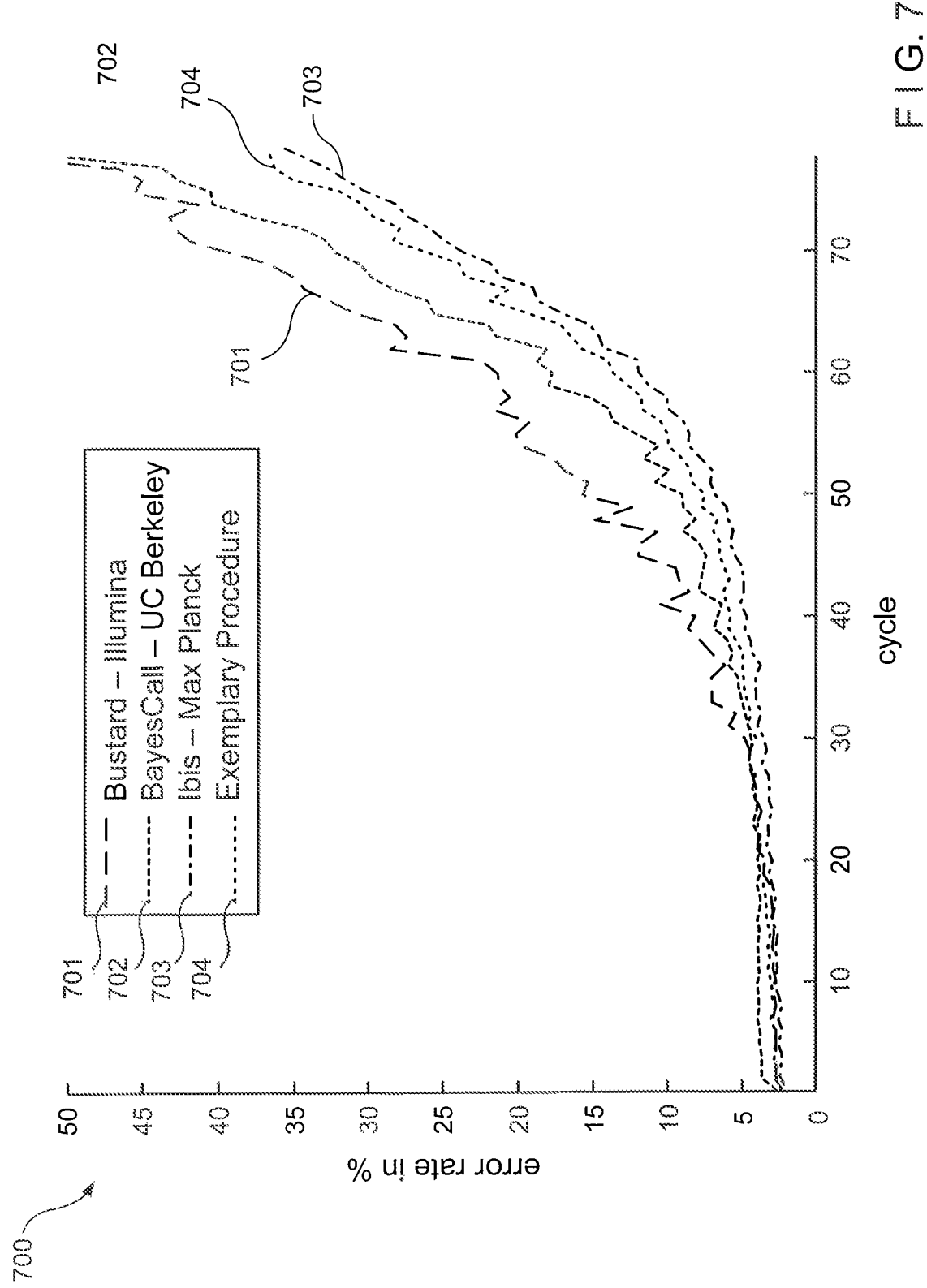
FIG. 7 is a graph showing an exemplary comparison of average error rates by cycle between an exemplary procedure in accordance with certain exemplary embodiments of the present disclosure and other base-caller procedures for the phi-x genome.

FIG. 7 shows a graph 700 illustrating an exemplary comparison of average error rates by cycle between an exemplary procedure in accordance with certain exemplary embodiments of the present disclosure and other base-caller procedures for the phi-x genome. For example, as shown in FIG. 7, lines 701-703 can represent error rates associated with certain procedures including Bustard (from Illumina), BayesCall (from University of California, Berkeley) and Ibis (from Max Planck), respectively. Line 704 can represent error rates associated with certain exemplary procedures according to the present disclosure. The error rates 701-704 shown in the graph 700 can be associated with an initial cycle and/or processing for the phi-x genome. As shown, while there can be a similar trend in the error rates between all four procedures, the error rates associated with the initial cycle and/or processing for the phi-x genome of the procedure according to the present disclosure can be more beneficial than the majority of others even without alignment scores being combined in accordance with certain exemplary embodiments of the present disclosure.

Figure 8:
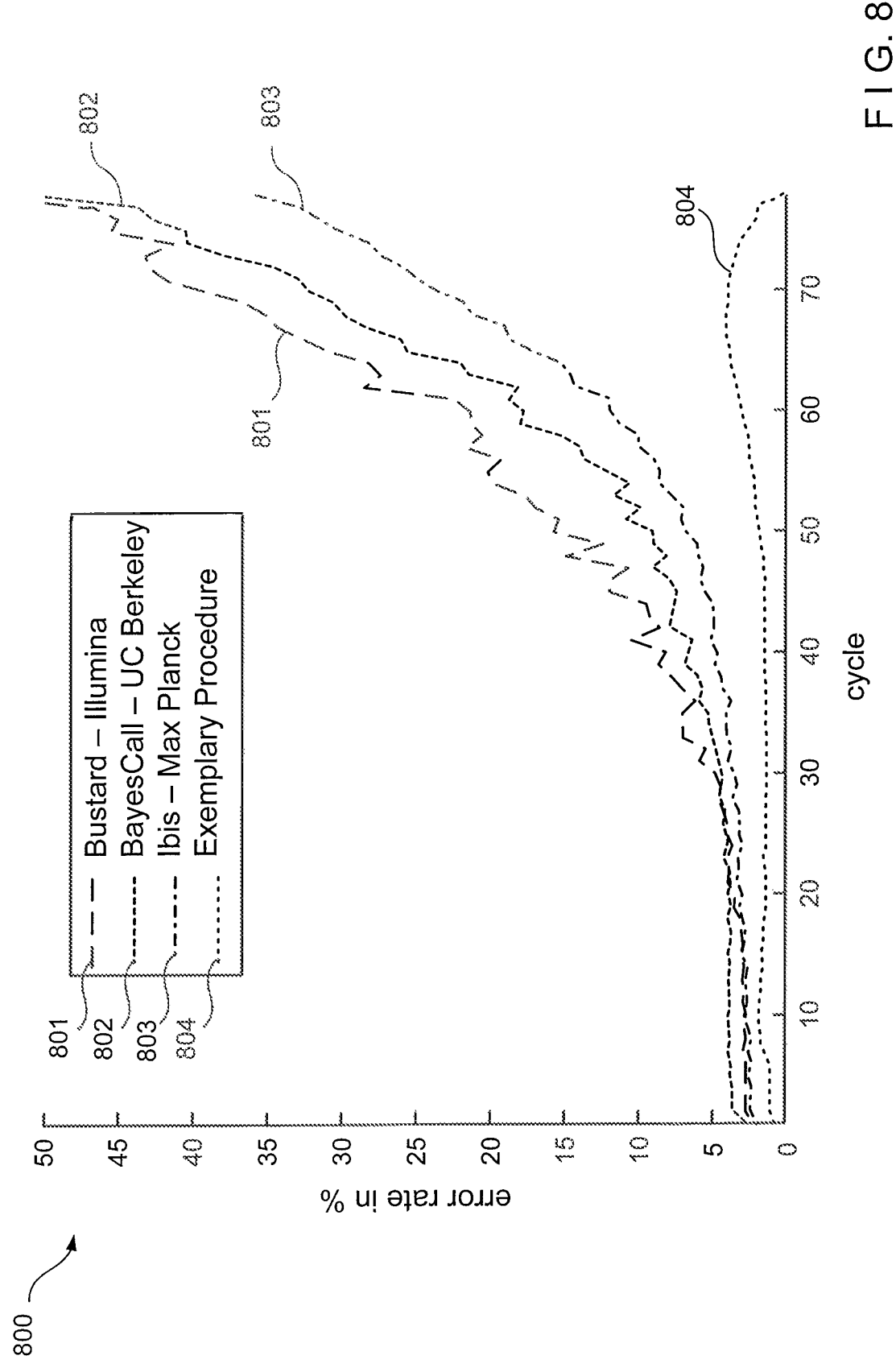
FIG. 8 is a graph showing an exemplary comparison of average error rates by cycle between an exemplary procedure in accordance with certain exemplary embodiments of the present disclosure and other base-caller procedures for the phi-x genome with base-calling and alignment scores being combined.

FIG. 8 shows a graph 800 illustrating an exemplary comparison of average error rates by cycle between the base-caller procedures of FIG. 8 and a procedure in accordance with certain exemplary embodiments of the present disclosure for the phi-x genome with both base-calling and alignment scores being combined according to certain exemplary embodiments of the present disclosure. For example, as shown in FIG. 8, lines 801-803 can represent error rates associated with the Bustard (from Illumina), BayesCall (from University of California, Berkeley) and Ibis (from Max Planck) procedures, respectively. The line 804 can represent error rates associated with certain exemplary procedures according to the present disclosure. As shown in FIG. 8, with the introduction of both base-calling and alignment scores being combined according to certain exemplary embodiments of the present disclosure, the error rates 804 of the exemplary procedure in accordance with the present disclosure can be significantly reduced, and likely be several times lower than the error rates 801-803 associated with the other procedures.

Figure 9:
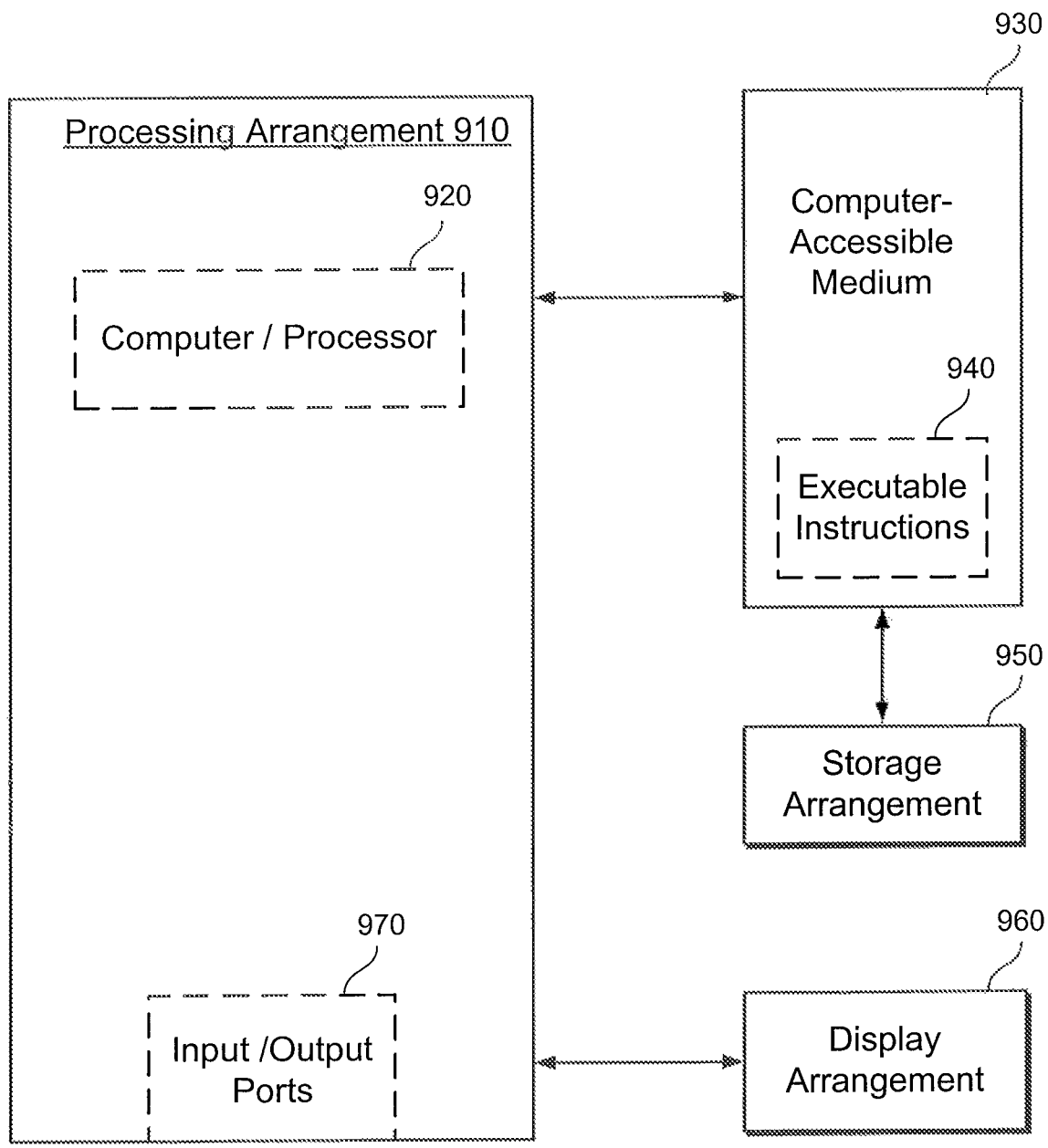
FIG. 9 is an exemplary block diagram of an exemplary system in accordance with certain exemplary embodiments of the present disclosure.

FIG. 9 shows an exemplary block diagram of an exemplary embodiment of a system according to the present disclosure. For example, an exemplary procedure in accordance with the present disclosure can be performed by a processing arrangement and/or a computing arrangement 910. Such processing/computing arrangement 910 can be, e.g., entirely or a part of, or include, but not limited to, a computer/processor 920 that can include, e.g., one or more microprocessors, and use instructions stored on a computer-accessible medium (e.g., RAM, ROM, hard drive, or other storage device).

As shown in FIG. 9, e.g., a computer-accessible medium 930 (e.g., as described herein above, a storage device such as a hard disk, floppy disk, memory stick, CD-ROM, RAM, ROM, etc., or a collection thereof) can be provided (e.g., in communication with the processing arrangement 910). The computer-accessible medium 930 can contain executable instructions 940 thereon. In addition or alternatively, a storage arrangement 950 can be provided separately from the computer-accessible medium 930, which can provide the instructions to the processing arrangement 910 so as to configure the processing arrangement to execute certain exemplary procedures, processes and methods, as described herein above, for example.

Further, the exemplary processing arrangement 910 can be provided with or include an input/output arrangement 970, which can include, e.g., a wired network, a wireless network, the internet, an intranet, a data collection probe, a sensor, etc. As shown in FIG. 9, the exemplary processing arrangement (computing arrangement) 910 can be in communication with an exemplary display arrangement 960, which, according to certain exemplary embodiments of the present disclosure, can be a touch-screen configured for inputting information to the processing arrangement in addition to outputting information from the processing arrangement, for example. Further, the exemplary display 960 and/or a storage arrangement 950 can be used to display and/or store data in a user-accessible format and/or user-readable format.

Figure 10:
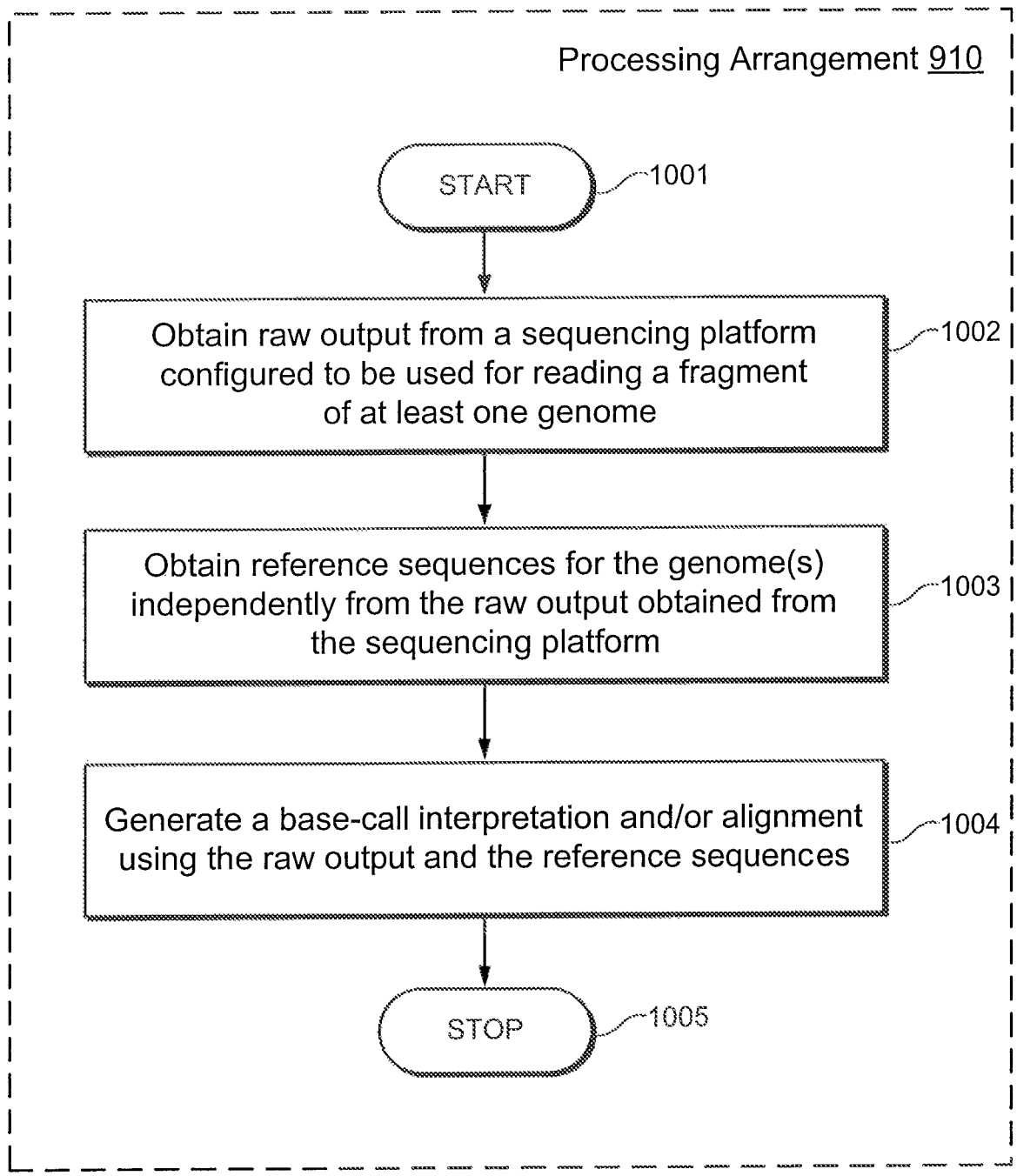
FIG. 10 is a flow diagram of an exemplary method in accordance with certain exemplary embodiments of the present disclosure.

FIG. 10 shows a flow diagram of a procedure in accordance with certain exemplary embodiments of the present disclosure. As shown in FIG. 10, the exemplary procedure can be executed on and/or by, e.g., the processing/computing arrangement 910 of FIG. 9. For example, starting at subprocess 1001, in accordance with certain exemplary embodiments of the present disclosure, the exemplary processing/computing arrangement 910 can, in subprocess 1002, obtain raw output from a sequencing platform configured to be used for reading a fragment of at least one genome. In subprocess 1003, the exemplary processing/computing arrangement 910 can obtain reference sequences for the genome(s) independently from the raw output obtained from the sequencing platform. Then, in accordance with certain exemplary embodiments of the present disclosure, in subprocess 1004, the exemplary processing/computing arrangement 910 can generate a base-call interpretation and/or alignment using the raw output and the reference sequences, for example.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly being incorporated herein in its entirety. All publications referenced above are incorporated herein by reference in their entireties.

What is claimed is:

1. A non-transitory computer-accessible medium having stored thereon computer executable instructions for assembling at least one genetic sequence which, when executed by a hardware processing arrangement, configure the hardware processing arrangement to:

(a) obtain a series of raw intensity outputs from a sequencing platform configured to (i) be used for reading a fragment of at least one genome and (ii) use a sequencing-by-ligation procedure, wherein each of the obtained raw intensity outputs comprises a plurality of randomly located short sequence reads, and wherein each of the randomly located short sequence reads has a read length of at least 48 base pairs (bps);

(b) obtain at least one reference sequence for the at least one genome, wherein the at least one reference sequence for the at least one genome is obtained independently from the series of first raw intensity outputs obtained from the sequencing platform;

(c) automatically generate a search tree comprising a plurality of nodes, wherein each of the plurality of nodes corresponds to a particular nucleotide base;

(d) automatically select a node of the plurality of nodes in the search tree;

(e) automatically expand the selected node by creating a plurality of child nodes, each of the plurality of child nodes corresponding to a particular further nucleotide base;

(f) automatically generate a score for one or more of the plurality of child nodes, wherein the score is a function of (i) at least one raw intensity output from the series of raw intensity outputs, (ii) the plurality of reference sequences, and (iii) the nucleotide base to which a particular one of the plurality of child nodes corresponds;

(g) automatically select one or more of the plurality of child nodes based on the score;

(h) automatically repeat procedures (e)-(g) for the selected child node;

(i) automatically generate a path through the plurality of nodes; and (j) automatically assemble the at least one genetic sequence based on the path.

2. The computer-accessible medium of claim 1, wherein the processing arrangement is further configured to:
automatically generate the score using a score function;
determine the score function based on information associated with a sequencing platform from which the series of raw intensity outputs are obtained; and
with the score function, analyze polymorphisms based on at least one of the raw intensity outputs or the reference sequences.

3. The computer-accessible medium of claim 1, wherein the sequencing platform is further configured to utilize at least one of a Sanger chemistry procedure or a sequencing-by-synthesis procedure.

4. The computer-accessible medium of claim 1, wherein the read length is at least 78 bps.

5. The computer-accessible medium of claim 1, wherein each of the raw intensity outputs further comprises at least one error associated with at least one of the plurality of randomly located short sequence reads.

6. The computer-accessible medium of claim 5, wherein the at least one error is related to at least one of an incorrect base-call, a missing base, one or more inserted bases, one or more deleted bases, or a homopolymeric compression.

7. The computer-accessible medium of claim 1, wherein the at least one genome comprises a genome from at least one of (i) one or more diseased cells, (ii) one or more normal cells, (iii) at least one individual organism, (iv) at least one population, or (v) at least one ecological system.

8. The computer-accessible medium of claim 1, wherein the at least one reference sequence is obtained from at least one of (i) a mathematical model, (ii) existing data, (iii) genomic single-molecules, or (iv) genomic materials that are at least one of amplified or otherwise modified.

9. The computer-accessible medium of claim 2, wherein the analyzing procedure comprises a branch-and-bound process.

10. The computer-accessible medium of claim 1, wherein the processing arrangement is further configured to generate the score based on an alignment between the raw intensity outputs and the at least one reference sequence.

11. The computer-accessible medium of claim 10, wherein the alignment includes determining, with the processing arrangement, if any of the raw intensity outputs is contained are within the reference sequences.

12. A method for assembling at least one genetic sequence, comprising:

(a) obtaining a series of raw intensity outputs from a sequencing platform configured to (i) be used for reading a fragment of at least one genome and (ii) use a sequencing-by-ligation procedure, wherein each of the obtained raw intensity outputs comprises a plurality of randomly located short sequence reads, and wherein each of the randomly located short sequence reads has a read length of at least 48 base pairs (bps);

(b) obtaining at least one reference sequence for the at least one genome, wherein the at least one reference sequence for the at least one genome is obtained independently from the series of raw intensity outputs obtained from the sequencing platform;

(c) automatically generating a search tree comprising a plurality of nodes, wherein each of the plurality of nodes corresponds to a particular nucleotide base;

(d) automatically selecting a node of the plurality of nodes in the search tree;

(e) automatically expanding the selected node by creating a plurality of child nodes, each of the child nodes corresponding to a particular further nucleotide base;

(f) automatically generating a score for one or more of the child nodes, wherein the score is a function of (i) at least one raw intensity output from the series of raw intensity outputs, (ii) the plurality of reference sequences, and (iii) the nucleotide base to which a particular one of the plurality of child nodes corresponds;

(g) automatically selecting one or more of the plurality of child nodes based on the score;

(h) automatically repeating procedures (e)-(g) for the selected child node;

(i) automatically generating a path through the plurality of nodes; and (j) using a computer hardware arrangement, automatically assembling the at least one genetic sequence based on the path.

13. The method of claim 12, further comprising:
automatically generating the score using a score function;
automatically determining the score function based on information associated with a sequencing platform from which the series of raw intensity outputs are obtained; and
with the score function, automatically analyzing polymorphisms based on at least one of the raw intensity outputs or the reference sequences.

14. The method of claim 12, wherein the sequencing platform is further configured to utilize at least one of a Sanger chemistry procedure or a sequencing-by-synthesis procedure.

15. The method of claim 12, wherein the read length is at least 78 bps.

16. The method of claim 12, wherein each of the raw intensity outputs further comprises at least one error associated with at least one of the plurality of randomly located short sequence reads.

17. The method of claim 16, wherein the at least one error is related to at least one of an incorrect base-call, a missing base, one or more inserted bases, one or more deleted bases, or a homopolymeric compression.

18. The method of claim 12, wherein the at least one genome comprises a genome from at least one of (i) one or more diseased cells, (ii) one or more normal cells, (iii) at least one individual organism, (iv) at least one population, or (v) at least one ecological system.

19. The method of claim 12, wherein the at least one reference sequence is obtained from at least one of (i) a mathematical model, (ii) existing data, (iii) genomic single-molecules, or (iv) genomic materials that are at least one of amplified or otherwise modified.

20. The method of claim 15, wherein the analyzing procedure comprises a branch-and-bound process.

21. The method of claim 12, further comprising at least one of displaying or storing information associated with the generated score in a storage arrangement in at least one of a user-accessible format or a user-readable format.

22. The method of claim 12, further comprising automatically generating the score based on an alignment between the raw intensity outputs and the at least one reference sequence.

23. The method of claim 22, wherein the alignment includes automatically determining if any of the raw intensity outputs is contained are within the reference sequences.

24. A system for assembling at least one genetic sequence, comprising:
a computer hardware arrangement configured to:
(a) obtain a series of raw intensity outputs from a sequencing platform configured to (i) be used for reading a fragment of at least one genome and (ii) use a sequencing-by-ligation procedure, wherein each of the obtained raw intensity outputs comprises a plurality of randomly located short sequence reads, and wherein each of the randomly located short sequence reads has a read length of at least 48 base pairs (bps);
(b) obtain at least one reference sequence for the at least one genome, wherein the at least one reference sequence for the at least one genome is obtained independently from the series of raw intensity outputs obtained from the sequencing platform;
(c) automatically generate a search tree comprising a plurality of nodes, wherein each of the plurality of nodes corresponds to a particular nucleotide base;
(d) automatically select a node of the plurality of nodes in the search tree;
(e) automatically expand the selected node by creating a plurality of child nodes, each of the child nodes corresponding to a particular further nucleotide base;
(f) automatically generate a score for one or more of the child nodes, wherein the score is a function of (i) at least one raw intensity output from the series of raw intensity outputs, (ii) the plurality of reference sequences, and (iii) the nucleotide base to which a particular one of the plurality of child nodes corresponds;
(g) automatically select one or more of the plurality of child nodes based on the score;
(h) automatically repeat procedures (e)-(g) for the selected child node;
(i) automatically generate a path through the plurality of nodes; and
(j) automatically assemble the at least one genetic sequence based on the path.

25. The system of claim 24, wherein the computer hardware arrangement is further configured to:
automatically generate the score using a score function;
automatically determine the score function based on information associated with a sequencing platform from which the series of raw intensity outputs are obtained; and
with the score function, automatically analyze polymorphisms based on at least one of the raw intensity outputs or the reference sequences.

26. The system of claim 24, wherein the sequencing platform is further configured to utilize at least one of a Sanger chemistry procedure or a sequencing-by-synthesis procedure.

27. The system of claim 24, wherein the read length is at least 78 bps.

28. The system of claim 24, wherein each of the raw intensity outputs further comprises at least one error associated with at least one of the plurality of randomly located short sequence reads.

29. The system of claim 28, wherein the at least one error is related to at least one of an incorrect base-call, a missing base, one or more inserted bases, one or more deleted bases, or a homopolymeric compression.

30. The system of claim 24, wherein the at least one genome comprises a genome from at least one of (i) one or more diseased cells, (ii) one or more normal cells, (iii) at least one individual organism, (iv) at least one population, or (v) at least one ecological system.

31. The system of claim 24, wherein the at least one reference sequence is obtained from at least one of (i) a mathematical model, (ii) existing data, (iii) genomic single-molecules, or (iv) genomic materials that are at least one of amplified or otherwise modified.

32. The system of claim 25, wherein the analyzing procedure comprises a branch-and-bound process.

33. The system of claim 24, wherein the computer hardware arrangement is further configured to automatically generate the score based on an alignment between the raw intensity outputs and the at least one reference sequence.

34. The system of claim 33, wherein the alignment includes automatically determining, using the computer hardware arrangement, if any of the raw intensity outputs is contained are within the reference sequences.

35. The computer-accessible medium of claim 1, wherein the read length is at least 100 bps.

36. The method of claim 12, wherein the read length is at least 100 bps.

37. The system of claim 24, wherein the read length is at least 100 bps.

* * * * *

UNITED STATES PATENT AND TRADEMARK OFFICE
CERTIFICATE OF CORRECTION

| | |
|---|---|
| PATENT NO. | : 10,964,408 B2 |
| APPLICATION NO. | : 13/266662 |
| DATED | : March 30, 2021 |
| INVENTOR(S) | : Mishra et al. |

It is certified that error appears in the above-identified patent and that said Letters Patent is hereby corrected as shown below:

In the Specification

Amend the Statement Regarding Federally Sponsored Research paragraph, under Column 1, Lines 20-26 with the following paragraph:
"This invention was made with government support under grant number R21 HG003714 awarded by the National Institutes of Health and under grant number CCF0836649 awarded by The National Science Foundation. Therefore, the government has certain rights in the invention."

Signed and Sealed this
Thirty-first Day of January, 2023

Katherine Kelly Vidal
*Director of the United States Patent and Trademark Office*